US007319090B2

(12) United States Patent
Katz

(10) Patent No.: US 7,319,090 B2
(45) Date of Patent: Jan. 15, 2008

(54) METHODS OF TREATING CEREBRAL ISCHEMIA

(75) Inventor: Laurence M. Katz, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 295 days.

(21) Appl. No.: 10/306,672

(22) Filed: Nov. 27, 2002

(65) Prior Publication Data

US 2004/0102368 A1    May 27, 2004

(51) Int. Cl.
*A61K 31/17* (2006.01)
*A61K 31/404* (2006.01)

(52) U.S. Cl. .......................... 514/12; 514/14; 514/415; 514/419

(58) Field of Classification Search .................... 514/2, 514/14, 415, 12, 413, 419
See application file for complete search history.

(56) References Cited

U.S. PATENT DOCUMENTS

| 6,214,790 B1 * | 4/2001 | Richelson et al. ............. 514/2 |
| 6,231,594 B1 | 5/2001 | Dae |
| 6,572,638 B1 | 6/2003 | Dae et al. |
| 6,582,457 B2 | 6/2003 | Dae et al. |
| 2004/0014651 A1 | 1/2004 | Richelson et al. |

OTHER PUBLICATIONS

"Nuerotensin-Induced Hypothemia Prevents Hipocampal Neuronal Damage and Increased Locomotor Activity Ischemic Gerbilis", Babcock et al., Brain Research Bulletin, 1993, 32(4), 373-8.*
"Animal Models of Focal and Global Cerebal Ischemia", Traystman, R., ILAR Journal, vol. 44, No. 2, 2003.*
"Therapeutic Hypothermia for Severe Traumatic Brain Injury", Kochanek et al., JAMA, Jun. 11, 2003, vol. 289, No. 22, Reprint.*
Katz, Laurence, et al., "Neurotensin Analog NT69L Induces Rapid and Prolonged Hypothermia after Hypoxic Ischemia", Academic Emergency Medicine vol. 8, No. 12: 1115-1121, Dec. 2001.
Katz, Laurence, et al., "Neurotensin Analog Induces Rapid and Prolonged Hypothermia after Cerebral Ischemia", Academic Emergency Medicine vol. 7, No. 5: 425, 2000.
Griffith, B.D., et al., "Induction of Brain Hypothemia by a Neurotensin Analog in Awake Rats", displayed at the 25th International Stroke Conference—New Orleans, LA, American Heart Association, Feb. 10-12, 2000.
Banks, William, et al., "Permeability of the blood-brain barrier to the nuerotensin$_{8-13}$ analog NT1", Brain Research vol. 695: 59-63, 1995.
Benmoussa, M., et al., "Low Doses of Neurotensin in the Preoptic Area Produce Hyperthermia. Comparison With Other Brain Sites and With Neurotensin-Induced Analgesia", Brian Research Bulletin vol. 39, No. 5: 275-279, 1996.
Bernard, S. et al., "Treatment of Comatose Survivors of Out-of-Hospital Cardiac with Induced Hypothermia", New Engl. J. Med. vol. 349, No. 8: 557-563, Feb. 21, 2002.

Bleyaert, A., et al., "Effect of postcirculatory-arrest life-support on neurological recovery in monkeys", Critical Care Medicine vol. 8, No. 3: 153-156, 1980.
Clifton, G., et al., "Lack of Effect of Induction of Hypothermia after Acute Brain Injury", The New England J. Med. vol. 344, No. 8: 556-563, Feb. 22, 2001.
Coimbra, C., et al., "Moderate hypothermia mitigates neuronal damage in the rat brain when initiated several hours following transient cerebral ischemia", Acta Neuropathologica vol. 87, No. 4: 325-331, 1994.
Colbourne, F., et al., "Delayed Postischemic Hypothermia: a Six Month Survial Study Using Behavioral and Histological Assessments of Neuroprotection", The Journal of Neuroscience vol. 15, No. 11: 7250-7260, 1995.
Colbourne, F., et al., "Postischemic Hypothermia. A Critical Appraisal with Implications for Clinical Treatment", Molecular Neurobiology vol. 14, 171-201, 1997.
Cusack, Bernadette, et al., "Effects of a novel neurotensin peptide analog given extacranially on CNS behaviors mediated by apomorphine and haloperidol", Brain Research vol. 856: 48-54, 2000.
Globus, M., et al., "Excitoxic index—a biochemical marker of selective vulnerability", Neuroscience Letters vol. 127: 39-42, 1991.
Gordon, C.J., "A review of terms and proposed nomenclature for regulated vs. forced, neurochemical-induced changes in body temperature", Life Sciences vol. 32: 1285-1295, 1983.
Gordon, C.J. et al., "Dynamics of behaviroal thermoregulation in the rat", Amer. J. Physiol. 261: R705-R711, 1991.
Gordon, C.J., The role of behaviroal thermoregulation as a thermoeffector during prolonged hypoxla in the rat, J. Thermal Biol. vol. 22: 315-324, 1997.
Gordon, C.J., "The therapeutic potential of regulated hypothermia", Emergency Medicine Journal, vol. 18: 81-89, 2001.
Gordon, C.J., "24-hour control of body temperature in rats: I. Integration of behavioral and autonomic effectors", Amer. J. Physiol. vol. 261: R71-R77, 1994.
Gunn, A., et al., "Selective Head Cooling in New Born Infants after Perinatal Asphyxia: a Safety Study", Pediatrics vol. 102, No. 4: 885-892, Oct. 1998.
Gunn, A., et al., "Should We Try to Prevent Hypothermia after Cardiac Arrest?", Pediatrics vol. 106, No. 1: 132-133 Jul. 2000.
Handler, C.M., et al., "Interaction betw en Opioid Agonists and Neurotensin on Thermoregulation in the Rat. I. Body Temperature", J. Pharmacology and Exp. Ther. vol. 274, No. 1: 284-292, 1995.
Hickey, R., et al., "Delayed, spontaneous hypothermia reduces neuronal damage after asphyxial cardiac arrest in rats", Critical Care Medicine vol. 28, No. 10: 3511-3516, Oct. 2000.

(Continued)

*Primary Examiner*—Brian Kwon
(74) *Attorney, Agent, or Firm*—Alston & Bird LLP

(57) ABSTRACT

The present invention provides methods of treating cerebral ischemia in mammals comprising inducing hypothermia in a mammal before, during, or following cerebral ischemia in the mammal. The hypothermia is induced by administering to the mammal an effective dose of a neurotensin analog that is capable of crossing the blood-brain barrier and that comprises neo-tryptophan.

26 Claims, 14 Drawing Sheets

OTHER PUBLICATIONS

Hickey, R., et al., "Use of Morris Water Maze and Acoustic Startle Chamber to Evaluate Neurologic Injury after Asphyxial Arrest in Rats", Pediatric Research vol. 39, No. 1: 77-84, 1996.

Hochachka, P.W., "Defense Strategies Against Hypoxia and Hypothermia", Science vol. 231: 234-241, Jan. 17, 1986.

Kammersgaard, L.P., et al., "Feasibility and Safety of Inducing Modest Hypothermia in Awake Patients with Acute Stroke Through Surface Cooling: A Case-Control Study", Stroke: 2251-2256, Sep. 2000.

Katz, Laurence, et al., "Outcome Model of Asphyxial Cardiac Arrest in Rats", Journal of Cerebral Blood Flow and Metabolism vol. 15, No. 6: 1032-1039, 1995.

Kraig R., et al., "Hydrogen Ions Kill Brain at Concentrations Reached in Ischemia", Journal of Cerebral Blood Flow and Metabolism vol. 7, No. 4: 379-386, 1987.

Kuboyama, K., et al., "Delaying cooling negates the beneficial effect of mild resuscitative cerebral hypothermia after cardiac arrest in dogs: A prospective, randomized study", Critical Care Medicine vol. 21, No. 9: 1348-1358, 1993.

Marion, D., et al., "Resuscitative hypothermia", Critical Care Medicine vol. 24, No. 2 (Suppl.): S81-S89, 1996.

Marion, D., et al., "Treatment of Traumatic Brain Injury with Moderate Hypothermia", The New England Journal of Medicine vol. 336, No. 8: 540-546, Feb. 20, 1997.

Morris, G.M., et al., "Place navigation impaired in rats with hippocampal lesions", Nature vol. 297: 681-685, Jun. 1982.

Muchlinski, et al, "The Concentrations for Four Neuropeptides in Various Brain Areas of Summer Active and Hibernating *Spermophilus Lateralis*", Comp. Biochem. Physiol. C. Toxicol. Pharmacol. vol. 74: 185-189, 1982.

Negovsky, Vladimir, "Postresuscitation disease", Critical Care Medicine vol. 16, No. 10: 942-946, Oct. 1988.

Prange, A.J., Jr., et al., "Neurotensin: Distribution of Hypothermic Response in Mammalian and Submammalian Vertebrates", Pharmacol. Biochem. Behav. vol. 11: 473-477, 1979.

Pulsinelli, William, et al., "Temporal Profile of Neuronal Damage in a Model of Transient Forebrain Ischemia", Annals of Neurology vol. 11, No. 5: 491-498, May 1982.

Sallmen, Tina, et al., "Major Changes in the Brain Histamine System of the Ground Squirrel *Citellus lateralis* during Hibernation", The Journal of Neuroscience vol. 19, No. 5: 1824-1835, Mar. 1, 1999.

Smith, Charles, et al., "Preventing Hypothermia: Convective and Intravenous Fluid Warming *Versus* Convective Warming Alone", J. Clin. Anesth., vol. 10: 380-385, Aug. 1998.

Tagami, M., et al., "Insulin-Like Growth Factor-1 Attenuates Apoptosis in Hippocampal Neurons Caused by Cerebral Ischemia and Reperfusion in Stroke-Prone Spontaneously Hypertensive Rats", Laboratory Investigation vol. 76, No. 5: 613-617, May 1997.

The Hypothermia After Cardiac Arrest Study Group, "Mild Therapeutic Hypothermia to Improve the Neurologic Outcome After Cardiac Arrest", The New England Journal of Medicine vol. 346, No. 8: 549-556, Feb. 21, 2002.

Thornhill, Jim, et al, "Therapeutic implications of hypothermic and hyperthermic temperature conditions in stroke patients", Can. J. Physiol. Pharmacol. vol. 79: 254-261, 2001.

Tisherman, Samuel, et al, "Future directions for resuscitation research. V. Ultra-advanced life support", Resuscitation vol. 34: 281-293, 1997.

Traystman, Richard, et al., "Oxygen radical mechanisms of brain injury following ischemia and reperfusion", J. App. Physiol. vol. 71: 1185-1195, 1991.

Tyler, Beth, et al., "Evidence for additional neurotensin receptor subtypes: neurotensin analogs that distinguish between neurotensin-mediated hypothermia and antinociception", Brain Research vol. 792: 246-252, 1998.

Tyler-McMahon, Beth, et al., "Highly potent neurotensin analog that causes hypothermia and antinociception", European J. Pharmacol. vol. 390: 107-111, 2000.

Tyler, Beth, et al., "In vitro binding and CNS effects of novel neurotensin agonists that cross the blood-brain barrier", Neuropharmacology vol. 38: 1027-1034, 1999.

Xiao, Feng, et al., "Mild Protective and Resuscitative Hypothermia for Asphyxial Cardiac Arrest in Rats", American Journal of Emergency Medicine vol. 16, No. 1, Jan. 1998.

Xiaojiang, Xu, et al., "A mathematical model for human brain cooling during cold-water near-drowning", J. Appl. Physiol. vol. 86: 265-272, 1999.

Yamada, Mitsuhiko, et al., "Regulation of Daily Rhythm of Body Temperature By Neurotensin Receptor in Rats", Research Communications in Molecular Pathology and Pharmacology vol. 87, No. 3: 323-331, Mar. 1995.

Zeiner, Andrea, et al., "Mild Resuscitative Hypothermia to Improve Neurological Outcome After Cardiac Arrest, A Clinical Feasibility Trial", Stroke: 86-94, Jan. 2000.

J. M. Carney, "Acute Tryptophan Pretreatment Protects Against Behavioral Changes Caused by Cerebral Ischemia", *Neuroscience Letters*, 1986, vol. 66, No. 2, pp. 127-130 and Database CAPLUS on STN Online, No. 1986:4354484 (Abstract).

Katz et al., "Regulated Hypothermia Reduces Brain Oxidative Stress After Hypoxic-Ischemia", *Brain Research*, 2004, vol. 1017 (1, 2), pp. 85-91 and Database CAPLUS on STN Online, No. 2004:579079 (Abstract).

Gordon et al., "Neurotensin Analog NT77 Induces Regulated Hypothermia in the Rat", *Life Sciences*, 2003, vol. 73, No. 20, pp. 2611-2623 and Database CAPLUS on STN Online, No. 2003:74394 (Abstract).

* cited by examiner

Time after injection, hr

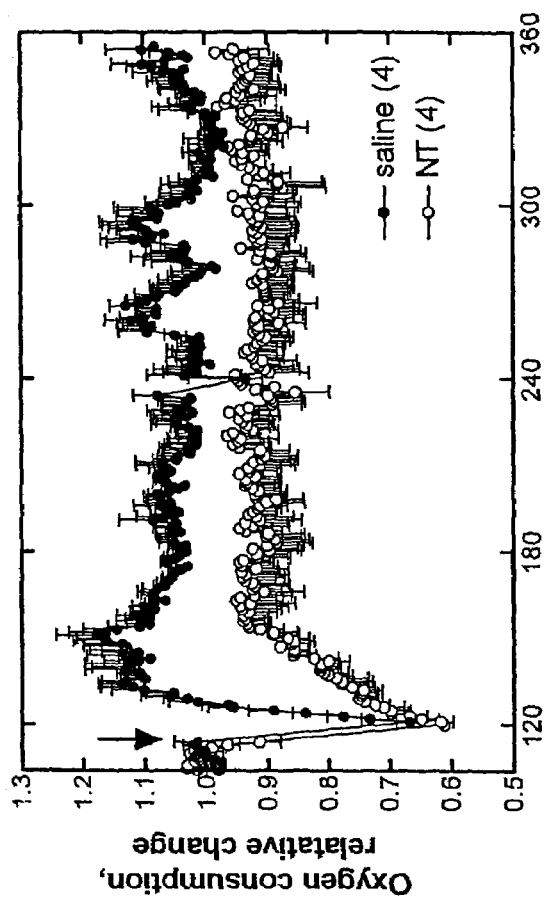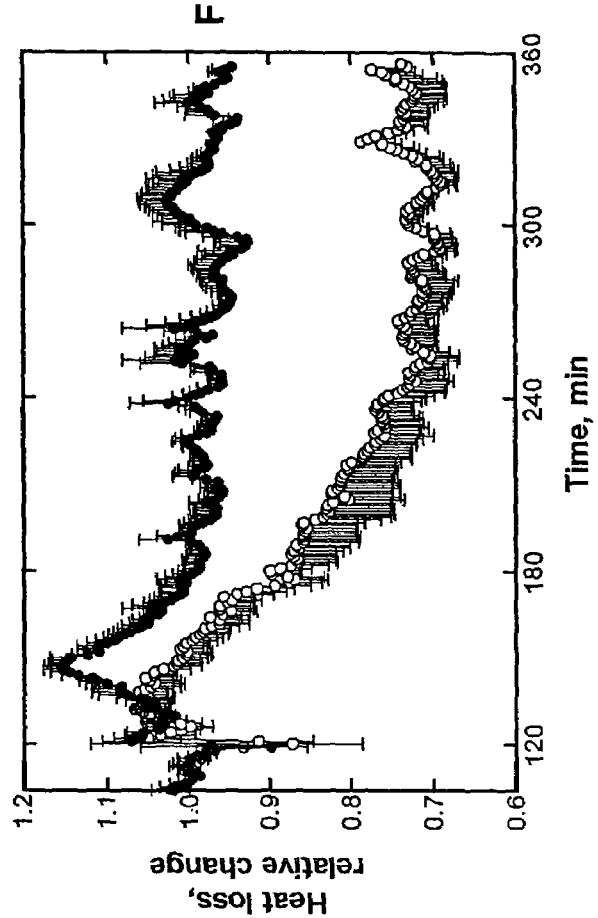

METHODS OF TREATING CEREBRAL ISCHEMIA

This work was supported by grant number 00508254U awarded by the American Heart Association.

FIELD OF THE INVENTION

The present invention generally relates to methods of treating cerebral ischemia in mammals.

BACKGROUND OF THE INVENTION

Cerebral ischemia (or brain ischemia) is a deficiency of blood supply to the brain. Cerebral ischemia can be caused by events such as cardiac arrest, traumatic brain injury, stroke, near drowning, birth asphyxia, drug overdose, and hypoxic encephalopathy. Cerebral ischemia can cause brain damage even if blood flow is restored to the brain, and such brain damage can occur after restoration of blood flow to the brain. For example, a component of brain damage from cardiac arrest may not appear to be histologically apparent for approximately 24 to 48 hours after resuscitation from cardiac arrest. This delayed brain damage is due to reperfusion disease (i.e., activation of pathological cascades that promote toxic free radical production, release of excitatory amino acids, severe acidosis, and other cellular and molecular changes).

A relatively new therapy for decreasing brain damage from cardiac arrest and other causes of cerebral ischemia is inducing mild hypothermia. The sooner hypothermia is induced after reperfusion, the more effective the therapy is in reducing brain damage (see, e.g., Coimbra et al., Moderate hypothermia mitigates neuronal damage in the rat brain when initiated several hours following transient cerebral ischemia, Acta. Neuropath., 1994, 87:325-331; The Hypothermia After Cardiac Arrest Study Group, Mild therapeutic hypothermia to improve the neurologic outcome after cardiac arrest, New Engl. J. Med., 2002; 346: 549-556; and Bernard et al., Treatment of comatose survivors of out-of-hospital cardiac arrest with induced hypothermia, New Engl. J. Med., 2002; 346: 557-563).

The most common method of inducing hypothermia is by the external application of ice. However, conductive cooling is a slow and inefficient method for promoting heat loss (see, e.g., Xu et al., A mathematical model for human brain cooling during cold-water near-drowning. J. Appl. Physiol., 1999, 86:265-272). Another way of inducing hypothermia after cardiac arrest is by performing a cardiopulmonary bypass. However, such a procedure cannot be initiated rapidly or outside of a hospital environment (see, e.g., Tisherman et al., Future directions for resuscitation research. V. Ultra-advanced life support. Resuscitation 1997; 34:281-93).

It would be advantageous to provide methods of treating cerebral ischemia that are less invasive than conventional procedures and can induce hypothermia more rapidly than conventional procedures.

SUMMARY OF THE INVENTION

The present invention generally relates to methods of treating cerebral ischemia in mammals. According to one aspect of the invention, a method of treating cerebral ischemia in a mammal is provided that comprises inducing hypothermia in a mammal before, during, or following cerebral ischemia in the mammal. The hypothermia is induced by administering to the mammal an effective dose of a neurotensin analog that is capable of crossing the blood-brain barrier and that comprises neo-tryptophan.

According to another aspect of the invention, a method of treating cerebral ischemia in a mammal is provided that comprises inducing regulated hypothermia in a mammal before, during, or following cerebral ischemia in the mammal. The regulated hypothermia is induced by administering to the mammal an effective dose of a neurotensin analog that is capable of crossing the blood-brain barrier and that comprises neo-tryptophan.

According to yet another aspect of the invention, a method of treating global cerebral ischemia in a mammal is provided that comprises inducing regulated hypothermia in a mammal during or following global cerebral ischemia in the mammal. The regulated hypothermia is induced by administering to the mammal an effective dose of a neurotensin analog selected from the group consisting of NT64D, NT64L, NT65L, NT66D, NT66L, NT67L, NT69L, NT69L', NT71, NT72, NT73, NT74, NT75, NT76, and NT77.

According to a further aspect of the invention, a method of treating focal cerebral ischemia in a mammal is provided that comprises inducing regulated hypothermia in a mammal during or following focal cerebral ischemia in the mammal. The regulated hypothermia is induced by administering to the mammal an effective dose of a neurotensin analog selected from the group consisting of NT64D, NT64L, NT65L, NT66D, NT66L, NT67L, NT69L, NT69L', NT71, NT72, NT73, NT74, NT75, NT76, and NT77.

**) show examples of how transient changes in selected $T_a$ precede small, transient changes in core temperature.

FIGS. 8A and 8B illustrate the relative change in oxygen consumption (FIG. 8A) and heat loss (FIG. 8B) of rats dosed with saline or NT77 based on measured values of oxygen consumption and heat loss averaged for the 15 minutes immediately prior to injection (see Example 2 below).

Figure 9A:
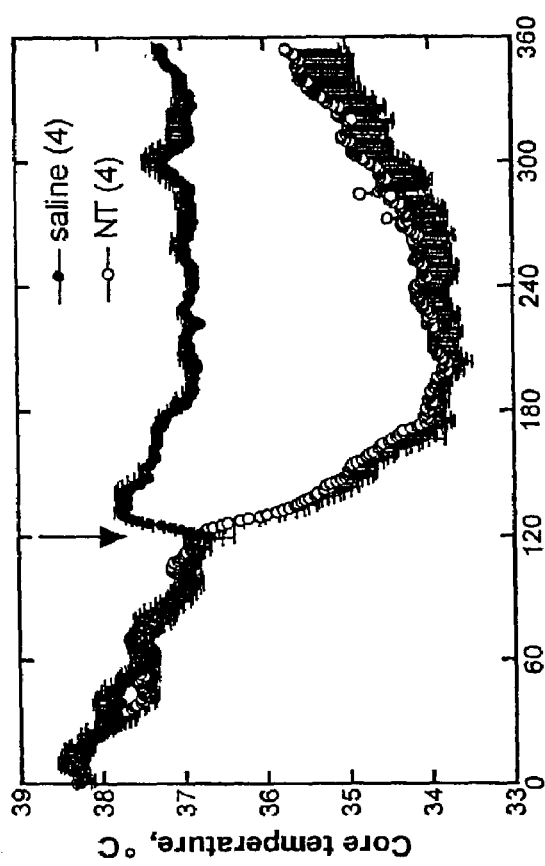
Figure 9B:
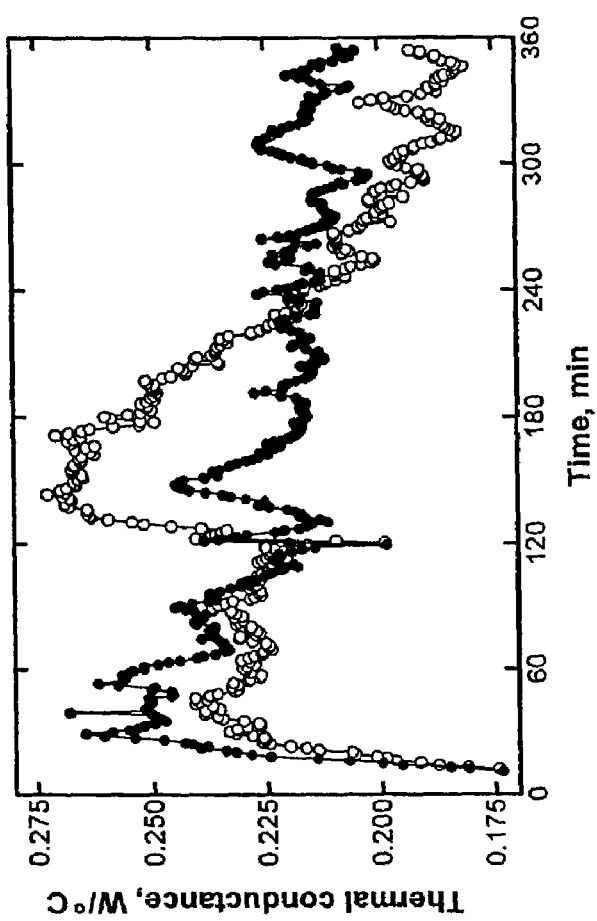

FIGS. 9A and 9B illustrate the relationship between core temperature (FIG. 9A) and dry thermal conductance (FIG. 9B) of rats housed in a calorimeter and injected with saline or NT77 (see Example 2 below).

Figure 10:
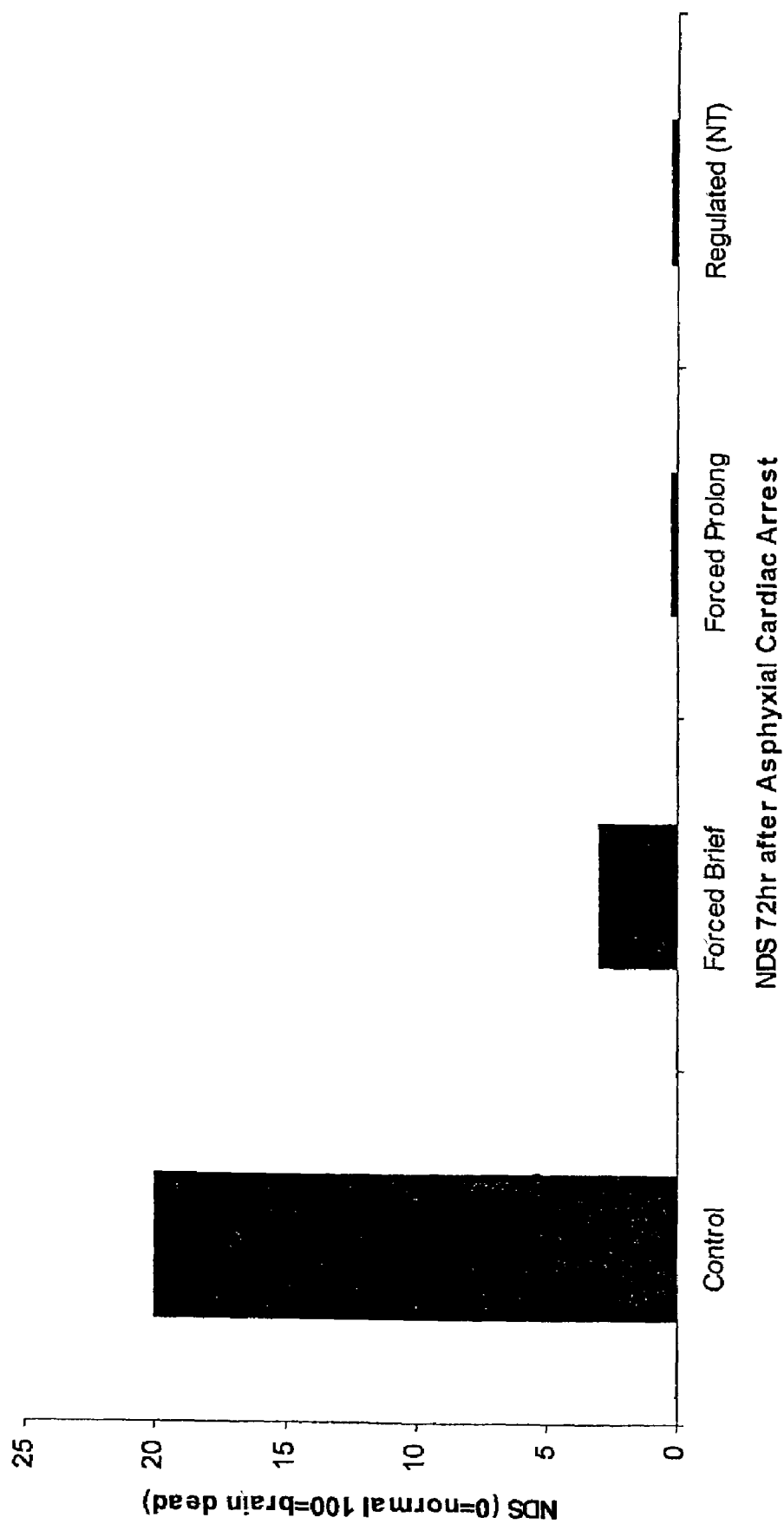

FIG. 10 illustrates a comparison of neurological deficit scores at 72 hours after asphyxial cardiac arrest in control, forced brief hypothermia, forced prolonged hypothermia, and regulated hypothermia (NT77) groups (see Example 3 below).

Figure 11:
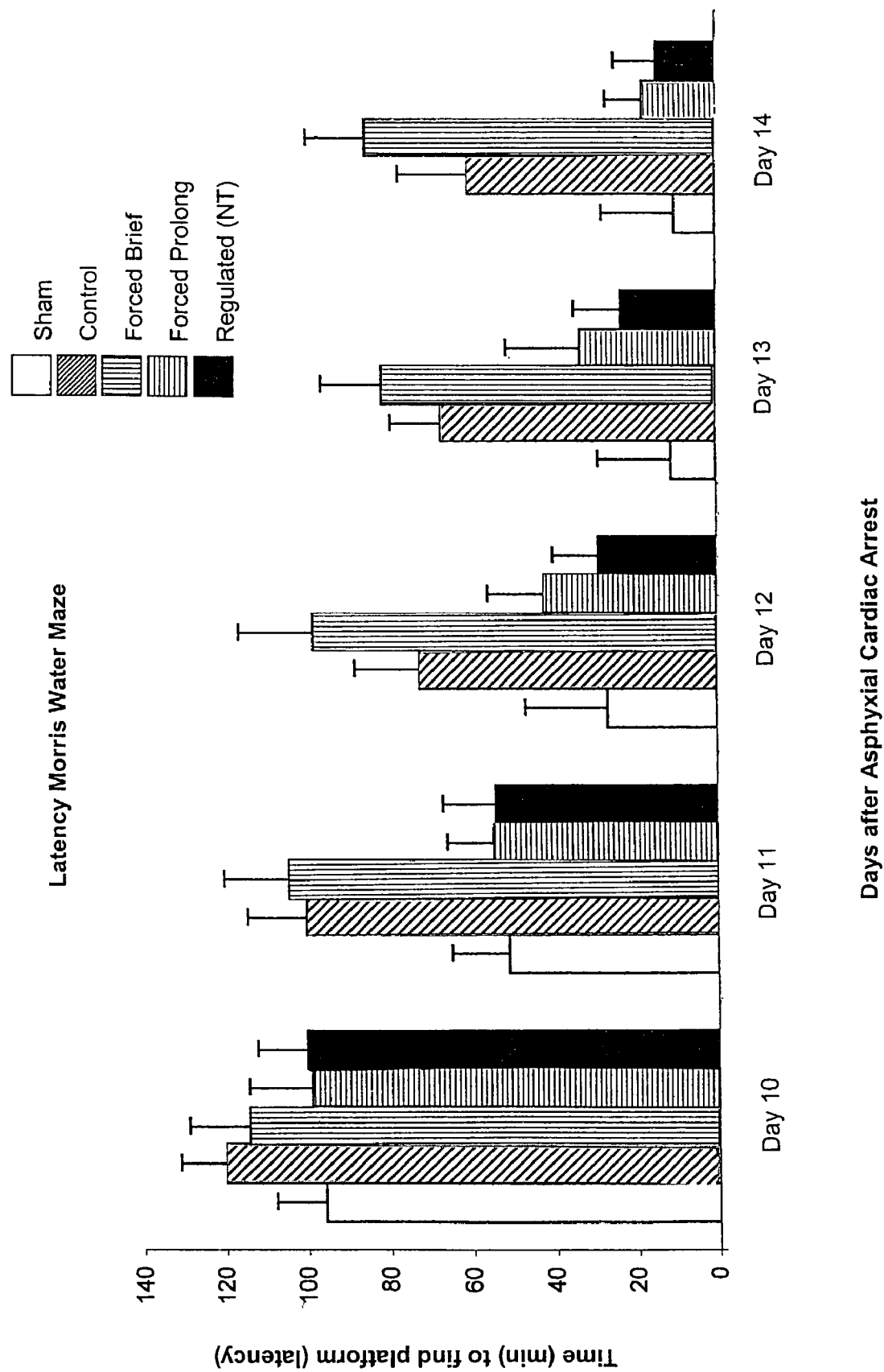

FIG. 11 shows a comparison of performance (i.e., latency time) in a Morris Water Maze on days 10-14 after asphyxial cardiac arrest for rats in a surgical sham group, a control group, a forced brief hypothermia group, a forced prolonged hypothermia group, and a NT77 group (see Example 3 below).

Figure 12:
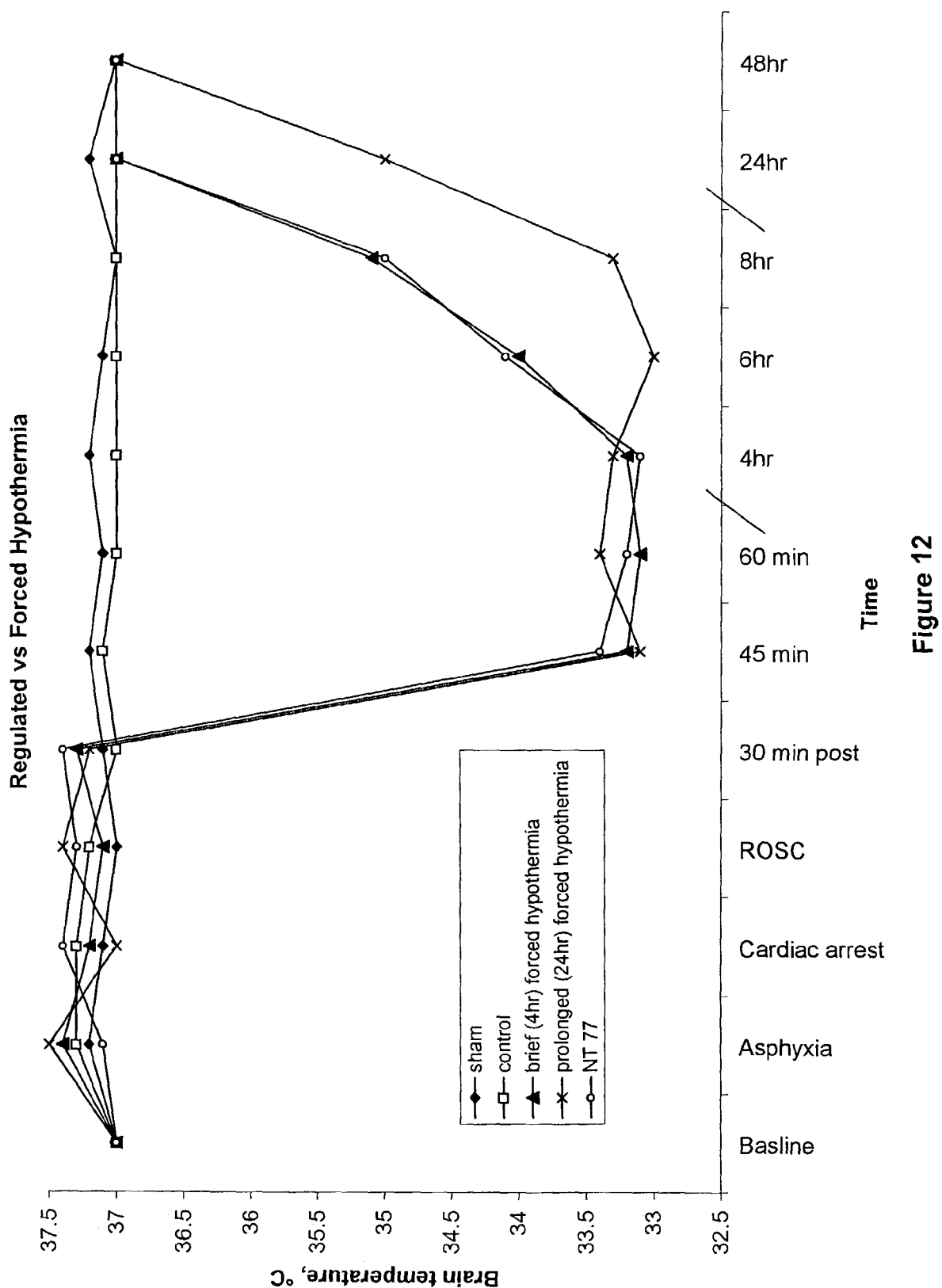

FIG. 12 is a comparison of brain temperature between sham, control, brief (4 hr) hypothermia, prolonged (24 hr) forced hypothermia, and NT77 group rats beginning at a baseline before cardiac arrest and extending to 48 hours after restoration of spontaneous circulation (see Example 3 below).

Figure 13:
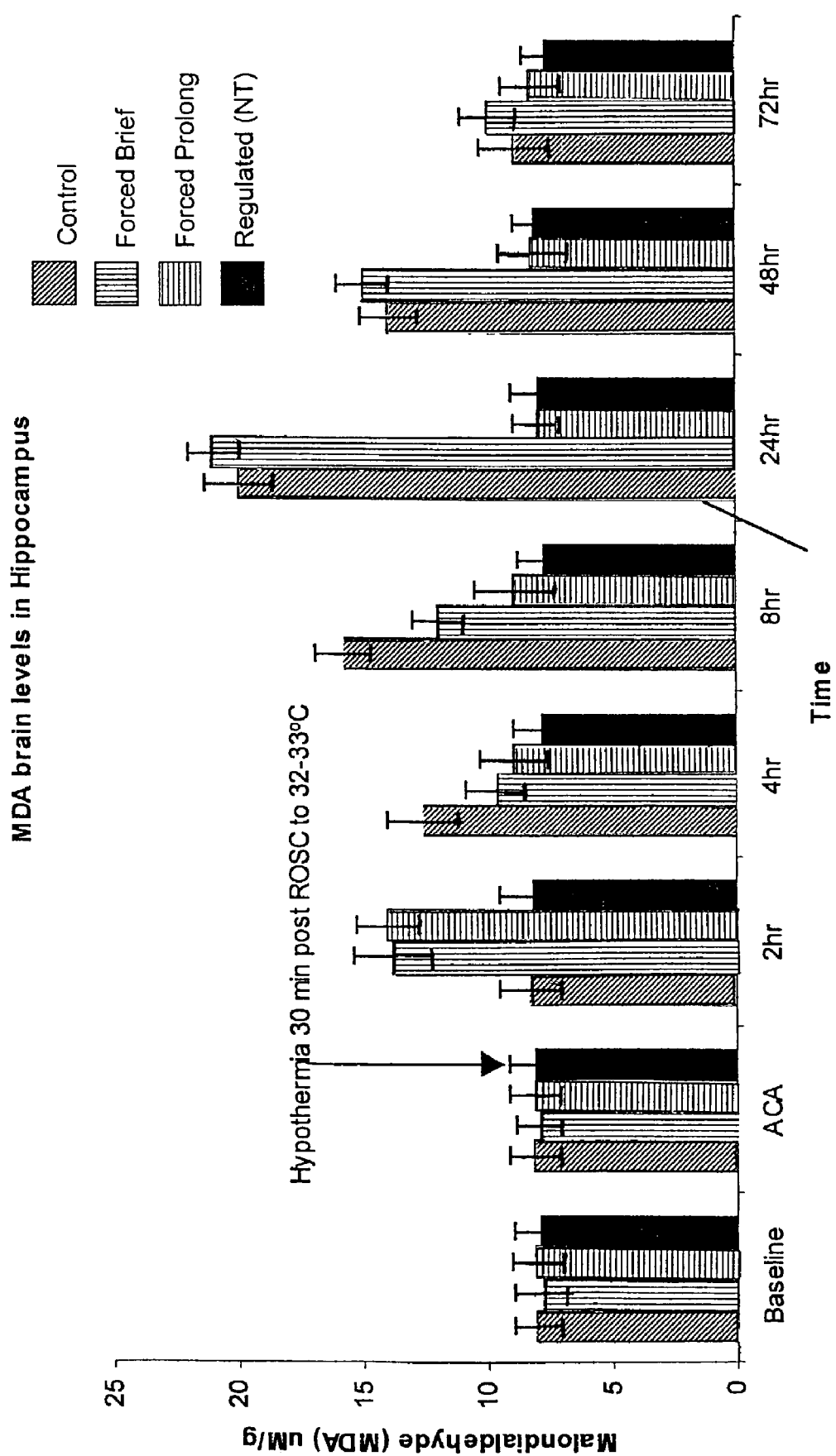

FIG. 13 illustrates the levels of malondialdehyde (MDA) in the hippocampus of rats in control, forced brief hypothermia, forced prolonged hypothermia, and regulated hypothermia (NT77) groups before and after asphyxial cardiac arrest (ACA) at the indicated time points (see Example 3 below).

DETAILED DESCRIPTION OF THE INVENTION

The present invention relates to methods of treating cerebral ischemia in mammals. Prior to describing this invention in further detail, however, the following terms will first be defined.

Definitions:

"Cerebral ischemia" means a deficiency of blood supply to the brain, and includes global and focal cerebral ischemia. As used herein, the phrase "brain damage from cerebral ischemia" means one or both of (1) brain damage incurred during cerebral ischemia and (2) brain damage incurred after blood supply to the brain has been restored (e.g., brain damage from reperfusion disease).

"Global cerebral ischemia" means a deficiency of blood supply to the entire brain.

"Focal cerebral ischemia" means a deficiency of blood supply to a portion of the brain.

"Hypothermia" means a condition in an organism where core body temperature is below normal core body temperature for the organism.

"Mild hypothermia" means a condition in an organism where core body temperature is about 2° C. to about 4° C. below normal core body temperature.

"Set-point temperature" or "set-point" means the value of core body temperature at which a healthy organism tends to stabilize by processes of thermoregulation such as heat gain, heat loss, and heat conservation.

"Forced hypothermia" means hypothermia that is induced by forcing the core body temperature of an organism below the normal level dictated by the set-point temperature.

"Regulated hypothermia" or "regulated hypothermic response" means hypothermia that is induced via a reduction in the set-point temperature of an organism.

"Neo-tryptophan" means 2-amino-3-[1H-indolyl]propanoic acid and includes both D-neo-tryptophan and L-neo-tryptophan. The chemical structure of neo-tryptophan is shown below as formula (I).

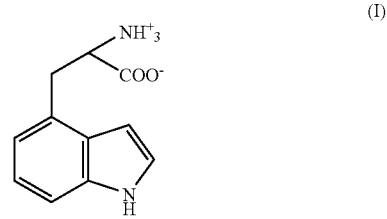

(I)

"Effective dose" means any amount of a neurotensin analog that prevents or reduces brain damage from cerebral ischemia in a recipient mammal that has suffered or is suffering from cerebral ischemia. An effective dose is preferably a dose that is not significantly toxic to the recipient mammal. The effective dose of a neurotensin analog may vary depending upon multiple factors including, but not limited to, the particular neurotensin analog, the type of mammal, the mammal's degree of illness, the mammal's weight, and the mammal's age. However, an effective dose of neurotensin analog will generally be from about 0.01 mg/kg body weight to about 1000 mg/kg body weight, although more or less amounts of neurotensin analog may be used.

"Neurotensin analog" means any polypeptide analog of neurotensin. A neurotensin analog may have an amino acid sequence that is longer, shorter, or the same length as the amino acid sequence of neurotensin. Neurotensin analogs may include non-naturally-occurring amino acids and may also include non-amino-acid compounds.

The present invention provides methods of treating cerebral ischemia in mammals in order to prevent or reduce brain damage due to cerebral ischemia. The methods comprise administering to a mammal (e.g., a rodent, a dog, a cat, a horse, a cow, a pig, a sheep, a goat, a non-human primate, a human, etc.) an effective dose of a neurotensin analog before, during, and/or following cerebral ischemia, including during reperfusion after cerebral ischemia. The neurotensin analog is preferably a neurotensin analog that is capable of crossing the blood-brain barrier in the mammal. The neurotensin analog also preferably comprises neo-tryptophan. Neurotensin analogs that may be administered to a mammal according to the methods described herein include, but are not limited to, NT64D, NT64L, NT65L, NT66D, NT66L, NT67L, NT69L, NT69L', NT71, NT72, NT73, NT74, NT75, NT76, and NT77.

The amino acid sequences of NT64D, NT64L, NT65L, NT66D, NT66L, NT67L, NT69L, NT69L', NT71, NT72, NT73, NT74, NT75, NT76, and NT77, methods of making these neurotensin analogs, and methods of making neo-tryptophan are described in U.S. Pat. No. 6,214,790, the entire content of which is hereby incorporated herein by reference. According to the patent, neo-tryptophan-containing neurotensin polypeptide analogs have enhanced biological effects as compared to neurotensin itself and such neurotensin polypeptide analogs can induce antinociception, hypothermia, thirst, weight loss, appetite suppression, and weight gain reduction. The patent states that incorporation of neo-tryptophan into a polypeptide sequence can create polypeptide analogs that exhibit increased biological activ ity, increased resistance to degradation by proteases, increased blood brain barrier permeability, improved binding affinities, and improved selectivity. Table 1, from U.S. Pat. No. 6,214,790 recites the amino acid sequences of NT, angiotensin, bradykinin, and leu-enkephalin polypeptides and polypeptide analogs, showing neo-tryptophan incorporated into polypeptides having biological and therapeutic interest.

TABLE I

Amino acid sequences of NT, angiotensin, bradykinin, and leu-enkephalin polypeptides and polypeptide analogs

| Polypeptide | 1 | 2 | 3 | 4 | 5 | 6 | 7 | 8 | 9 | 10 | 11 | 12 | 13 |
|---|---|---|---|---|---|---|---|---|---|---|---|---|---|
| NT (SEQ ID NO: 1) | p-Gln | L-Leu | L-Tyr | L-Glu | L-Asn | L-Lys | L-Pro | L-Arg | L-Arg | L-Pro | L-Tyr | L-Ile | L-Leu |
| NT (8-13) (SEQ ID NO: 2) | | | | | | | | L-Arg | L-Arg | L-Pro | L-Tyr | L-Ile | L-Leu |
| NT (9-13) (SEQ ID NO: 3) | | | | | | | | | L-Arg | L-Pro | L-Tyr | L-Ile | L-Leu |
| NTW (SEQ ID NO: 4) | | | | | | | | L-Arg | L-Arg | L-Pro | L-Trp | L-Ile | L-Leu |
| NT (tert-Leu) (SEQ ID NO: 5) | | | | | | | | L-Arg | L-Arg | L-Pro | L-Tyr | tert-Leu | L-Leu |
| Eisai* (SEQ ID NO: 6) | | | | | | | | N-methyl-Arg | L-Lys | L-Pro | L-Trp | tert-Leu | L-Leu |
| NT2 (SEQ ID) NO: 7) | | | | | | | | D-Lys | L-Arg | L-Pro | L-Tyr | L-Ile | L-Leu |
| NT24 "27" (SEQ ID NO: 8) | | | | | | | | L-Arg | D-Orn[&] | L-Pro | L-Tyr | L-Ile | L-Leu |
| NT34 (SEQ ID NO: 9) | | | | | | | | L-Arg | L-Arg | L-Pro | L-3,1'-Nal[#] | L-Ile | L-Leu |
| NT64D (SEQ ID NO: 10) | | | | | | | | L-Arg | L-Arg | L-Pro | D-neo-Trp | L-Ile | L-Leu |
| NT64L (SEQ ID NO: 11) | | | | | | | | L-Arg | L-Arg | L-Pro | L-neo-Trp | L-Ile | L-Leu |
| NT65L (SEQ ID NO: 12) | | | | | | | | L-Arg | L-Arg | L-Pro | L-neo-Trp | tert-Leu | L-Leu |
| NT66D (SEQ ID NO: 13) | | | | | | | | D-Lys | L-Arg | L-Pro | D-neo-Trp | tert-Leu | L-Leu |
| NT66L (SEQ ID NO: 14) | | | | | | | | D-Lys | L-Arg | L-Pro | L-neo-Trp | tert-Leu | L-Leu |
| NT67L (SEQ ID NO: 15) | | | | | | | | D-Lys | L-Arg | L-Pro | L-neo-Trp | L-Ile | L-Leu |
| NT69L (SEQ ID NO: 16) | | | | | | | | N-methyl-Arg | L-Lys | L-Pro | L-neo-Trp | tert-Leu | L-Leu |
| NT69L (SEQ ID NO: 17) | | | | | | | | N-methyl-Arg | L-Arg | L-Pro | L-neo-Trp | tert-Leu | L-Leu |
| NT71 (SEQ ID NO: 18) | | | | | | | | N-methyl-Arg | DAB[$] | L-Pro | L-neo-Trp | tert-Leu | L-Leu |
| NT72 (SEQ ID NO: 19) | | | | | | | | | D-Lys | L-Pro | L-neo-Trp | tert-Leu | L-Leu |
| NT73 (SEQ ID NO: 20) | | | | | | | | | D-Lys | L-Pro | L-neo-Trp | L-Ile | L-Leu |
| NT74 (SEQ ID NO: 21) | | | | | | | | | DAB | L-Pro | L-neo-Trp | tert-Leu | L-Leu |
| NT75 (SEQ ID NO: 22) | | | | | | | | | DAB | L-Pro | L-neo-Trp | L-Ile | L-Leu |
| NT76 (SEQ ID NO: 23) | | | | | | | | | L-Arg | D-Orn | L-Pro | L-neo-Trp | L-Ile | L-Leu |
| NY77 (SEQ ID NO: 24) | | | | | | | | | L-Arg | D-Orn | L-Pro | L-neo-Trp | tert-Leu | L-Leu |
| Angiotensin (SEQ ID NO: 25) | Asp | Arg | Val | Tyr | Ile | His | Pro | Phe | | | | | |
| Ang1 (SEQ ID NO: 26) | Asp | Arg | Val | L-neo-Trp | Ile | His | Pro | Phe | | | | | |
| Bradykinin (SEQ ID NO: 27) | Arg | Pro | Pro | Gly | Phe | Ser | Pro | Phe | Arg | | | | |
| Brdy1 (SEQ ID NO: 28) | Arg | Pro | Pro | Gly | L-neo-Trp | Ser | Pro | Phe | Arg | | | | |
| Leu-enkephalin (SEQ ID NO: 29) | Tyr | Gly | Gly | Phe | Leu | | | | | | | | |
| Lenk1 (SEQ ID NO: 30) | L-neo-Trp | Gly | Gly | Phe | Leu | | | | | | | | |

*Tsuchiya Y et al., (1989) European Patent Application 89104302.8;
[#]naphthalylalanine;
[$]diaminobutyric acid;
[&]D-ornithine The neurotensin analog may be administered to any part of the mammal's body, including, but not limited to, intestines, stomach, muscle tissues, blood stream, lungs, brain, nasal cavity, peritoneal cavity, and the like. The neurotensin analog may be administered to the mammal's body using any administration method such as, for example, by intravenous injection, intraarterial injection, intraperitoneal injection, intramuscular injection, subcutaneous injection, extracranial injection, intrathecal injection, intradermal injection, oral administration, and inhalation. The neurotensin analog to be administered may be in various forms, including aqueous or non-aqueous solutions, suspensions, or emulsions. The neurotensin analog is preferably in a sterile form. The neurotensin analog is typically administered as a single dose because of the tachyphylaxis that typically occurs after multiple doses. However, the neurotensin analog may be administered to the mammal more than once or at a specified frequency.

Without being limited by theory, it is believed that at least one factor of the therapeutic effect of the methods of treating cerebral ischemia in mammals described herein is that hypothermia is induced. Many studies have indicated or suggested that mild hypothermia provides protection to the pathological damage resulting from cerebral ischemia (see, e.g., Gordon, C. J., The therapeutic potential of regulated hypothermia, Emergency Medicine Journal 18, 81-89, 2001; Marion et al., Resuscitative hypothernia, Crit. Care Med 24:S81-89, 1996). Although the mechanisms of action of hypothermic protection after cerebral ischemia are not entirely understood, it is believed that hypothermia protects tissues deprived of oxygen by slowing the rate of cellular damage that occurs due to factors such as free radicals and tissue edema.

The specific therapeutic window of opportunity to induce hypothermia after cerebral ischemia is unknown. However, the more rapidly hypothermia is induced after a cerebral insult, the more effective the therapy (see, e.g., Coimbra et al., Moderate hypothermia mitigates neuronal damage in the rat brain when initiated several hours following transient cerebral ischemia, Acta. Neuropath., 1994; 87:325-331). Therefore, according to the present invention, when the neurotensin analog is administered to a mammal after onset of cerebral ischemia, hypothermia is induced as soon as possible, preferably within 4 hours after onset of cerebral ischemia, more preferably within 1 hour after onset of cerebral ischemia, and even more preferably within 30 minutes after onset of cerebral ischemia. In accordance therewith, when the neurotensin analog is administered to a mammal after onset of cerebral ischemia, the neurotensin analog is administered as soon possible after onset of cerebral ischemia, preferably within 4 hours after onset of cerebral ischemia, more preferably within 1 hour after cerebral ischemia, and even more preferably within 30 minutes after onset of cerebral ischemia. When the neurotensin analog is administered to a mammal following cerebral ischemia (i.e., after onset of reperfusion), the neurotensin analog is administered as soon possible after onset of reperfusion, preferably within 4 hours after onset of reperfusion, more preferably within 1 hour after onset of reperfusion, and even more preferably within 30 minutes after onset of reperfusion.

The rapidity with which a neurotensin analog induces hypothermia by the methods described herein may vary depending upon multiple factors, including the particular mammal that is treated, the particular neurotensin analog that is administered, and the method used to administer the neurotensin analog. Generally, a neurotensin analog induces hypothermia in the mammal within 30 minutes of administration of the neurotensin analog, preferably within 15 minutes of administration of the neurotensin analog, more preferably within 10 minutes of administration of the neurotensin analog. The length of the hypothermia induced by the methods described herein may also vary depending upon multiple factors, including the particular mammal that is treated and the particular neurotensin analog that is administered. Generally, the hypothermia induced by the methods of the present invention is at least 4 hours long, preferably at least 5 hours long, more preferably at least 6 long, and most preferably at least 24 hours long. Finally, the degree of hypothermia (i.e., the temperature variance from normal body temperature) may also vary depending upon multiple factors, including the particular mammal that is treated and the particular neurotensin analog that is administered. Generally, the hypothermia will reduce the core body temperature of a mammal that is treated from 1° C. to 10° C. below normal body temperature, preferably from 1.5° C. to 6° C. below normal body temperature, and most preferably from 2° C. to 4° C. below normal body temperature.

Again without being limited by theory, it is believed that the hypothermia induced by the methods of the present invention is regulated hypothermia. Reducing body temperature via a reduction in the set-point temperature of an organism (i.e., regulated hypothermia) is believed to provide a better method of achieving hypothermia to treat cerebral ischemia than conventional conductive heat loss. The conventional method of inducing hypothermia by external cooling forces body temperature below the normal level dictated by the set-point temperature; such forced hypothermia leads to physiological responses designed to maintain normothermia. These physiological responses may blunt or delay achieving the hypothermic temperature desired for treatment and have the potential to negate the therapeutic benefits of the hypothermic treatment by creating physiological and psychological stress. Regulated hypothermia, on the other hand, may reduce the potentially deleterious physiological stressors of conductive heat loss as well as improve patient comfort (see, e.g., Gordon, C. J. The therapeutic potential of regulated hypothermia. Emergency Medicine Journal, 18, 81-89, 2001).

The methods of the present invention offer several other advantages over conventional methods of inducing hypothermia. The methods of the present invention are easier to administer than conventional methods of cooling and require no special equipment such as a ventilator or the equipment needed for inducing hypothermia by performing cardiopulmonary bypass. Also, the methods of the present invention may not require the external warming of the mammal that is sometimes required after conventional forced hypothermia because the neurotensin analog will normally be metabolized by the mammal's body.

EXAMPLES

The invention will be further explained by the following illustrative examples that are intended to be non-limiting.

Example 1

Treatment of Hypoxic Ischemia Caused by Asphyxial Cardiac Arrest using Neurotensin Analog NT69L The purpose of this study was (1) to determine whether intravenous administration of the neurotensin analog NT69L to rats after resuscitation from asphyxial cardiac arrest would induce hypothermia and (2) to assess neurological outcome of rats injected with NT69L to determine whether NT69L administration after asphyxial cardiac arrest would reduce brain damage caused by the asphyxial cardiac arrest and reperfusion compared to rats not administered with NT69L.

I. Animal Subjects and Preparation

Sixteen male Sprague-Dawley rats (Harlan; Madison, Wis.) weighing 300±50 grams were randomized to a control group (saline) or treatment group (NT69L) after resuscitation from asphyxial cardiac arrest. The outcome model of asphyxial cardiac arrest in rats was used to induce the cerebral insult in all rats (Katz et al., Outcome model of asphyxial cardiac arrest in rats, J. Cereb. Blood Flow Metab., 1995, 15:1032-1039). Under titrated inhaled isoflurane anesthesia, brain telemetric probes (Mini-Mitter; Sunriver, Oreg.) were implanted three days before the cerebral insult. Asphyxial cardiac arrest and resuscitation in pilot experiments conducted earlier than three days after probe placement resulted in worsened outcome versus historic controls. On the day of the cerebral insult, rats were again anesthetized with inhaled isoflurane anesthesia, intubated, and mechanically ventilated. A tail artery was cannulated for continuous blood pressure monitoring and blood gas analysis, while the jugular vein was cannulated for intravenous drug administration. Intravenous vecuronium (2 mg/kg intravenous) and cessation of mechanical ventilation were used to induce apneic asphyxia. Asphyxia led to cardiac arrest (i.e., mean arterial pressure (MAP)<10 mm Hg and a pulse pressure of 0 mm Hg) within approximately 3 minutes; the cardiac arrest was maintained until resuscitation. Eight minutes after asphyxia, the rats were resuscitated with mechanical ventilation (100% oxygen), 0.005 mg/kg intravenous epinephrine, and chest compressions until a mean arterial pressure of 60 mm Hg was produced and maintained by a spontaneously beating heart for more than 10 seconds. Immediately after restoration of spontaneous circulation (ROSC), the rats were placed in an incubator that maintained an ambient temperature of 31.6° C. Pilot experiments in control rats showed that a precisely controlled, 50% humidified ambient temperature of 31.6° C. for 24 hours after ROSC maintained brain temperature at 37° C., while avoiding either hypothermia or hyperthermia. Ten minutes after ROSC, NT69L (0.5 mg/kg) 8 mL/kg or saline 3 mL/kg was administered intravenously. The ventilator was adjusted to normalize temperature-corrected arterial carbon dioxide before the insult and for two hours after ROSC. Two hours after ROSC, spontaneously breathing rats were extubated and maintained in the incubator for 24 hours. Rats were handled daily after the experiment and had free access to food and water.

In separate pilot experiments, four rats were instrumented for placement of temperature probes and intravenous catheters as described above. Three days after recovery from anesthesia, NT69L was administered intravenously to two free-roaming, unanesthetized rats at room temperature (23° C.). In the same environment and at the same time, two rats were given a similar volume of saline for comparison.

II. Measurements

On days 10-14 after ROSC, the rats were accessed for performance in a Morris Water Maze (MWM). Evaluation was begun on day 10 to ensure that there was complete recovery from anesthesia and the surgical procedures based on prior pilot studies (data not shown). A six foot diameter round pool was filled with water (26° C.) to a depth of 20 cm, 1 cm above an 11-cm diameter clear glass escape platform. The escape platform was invisible to a swimming rat and was placed in the northeast quadrant of the pool. The pool had large visible and distinct geometric shapes placed in a north, south, east, and west distribution on the side of the pool wall so that a swimming rat could easily visualize the orientation markers. The pool was situated in a room with black walls and ceiling to minimize external distractions for the rats. Rats were initially placed in the pool (without the escape platform) for 2 minutes to become acclimatized to the new swimming environment. The rats were then placed on the escape platform for 30 seconds to allow for self orientation in the pool. Next, the rats were randomly placed in each of the four geographic outer regions of the pool and their travel path, swim speed, and time required to locate the hidden platform (latency time) were recorded. Rats performed four swim trials on each day with a maximum swim time of 2 minutes, at which time the trial was terminated if a rat was unable to locate the platform. A 3-minute rest period was provided between trials. In addition to the rats that sustained cardiac arrest (n=16), nine sham rats were surgically instrumented and allowed to recover for ten days before being assessed for performance in the MWM.

Figure 1:
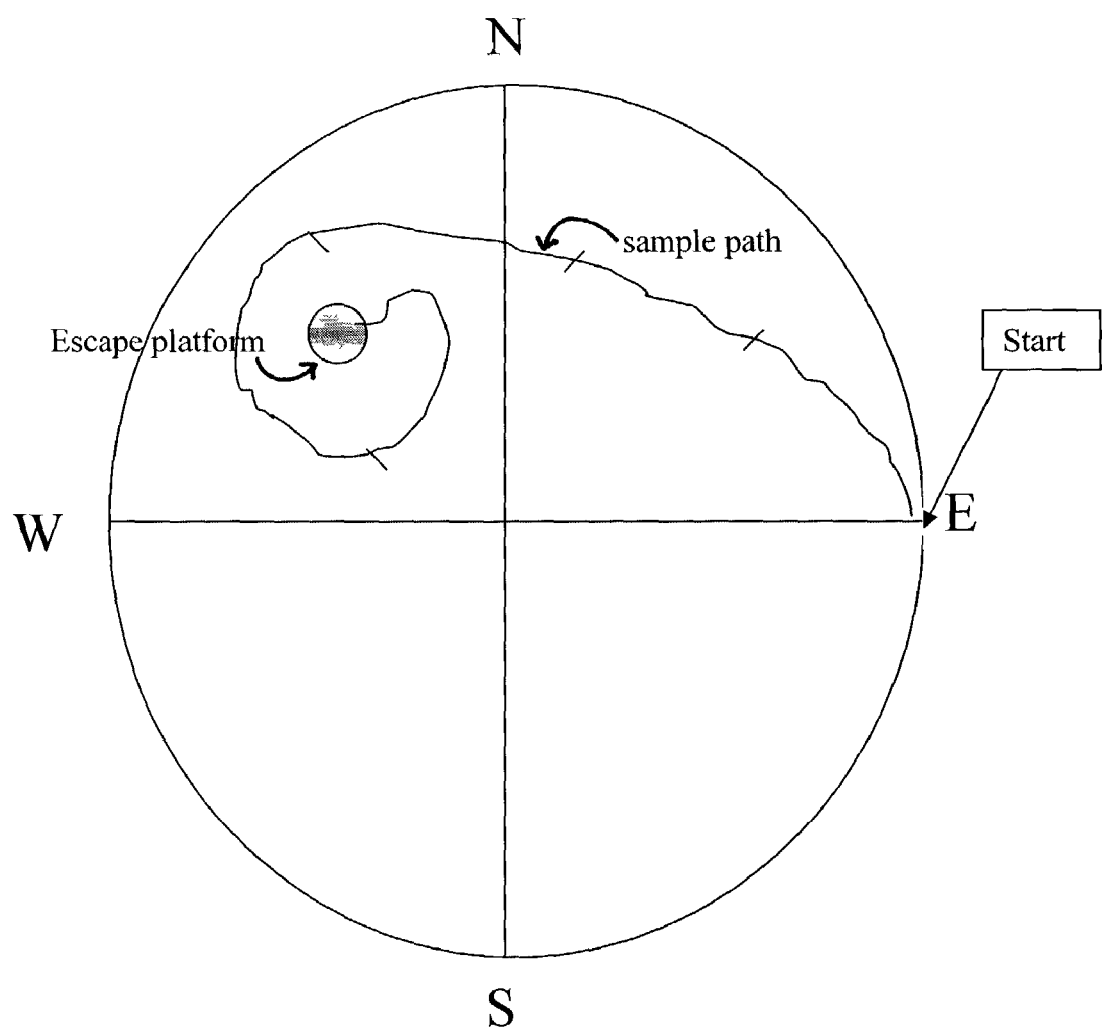
FIG. 1 illustrates the sample path of a NT69L group rat in a Morris Water Maze as described in Example 1 below.

FIG. 1 illustrates the sample path of a NT69L group rat in the Morris Water Maze on day 14 after resuscitation. Latency time was 9 seconds and distance traveled was 225 cm.

A final neurological deficit score (NDS) was performed 14 days after ROSC by an evaluator blinded to the insult and therapeutic intervention. Rats were tested for coordination (balance beam walk placing test, depth perception, righting reflex) and for motor and sensory function as described in Katz et al., Outcome model of asphyxial cardiac arrest in rats, J. Cereb. Blood Flow Metab., 1995, 15:1032-1039. The NDS includes a range from 0 (indicating normal) to 100 (indicating brain dead).

III. Data Analysis

Physiological variables (arterial blood gas, glucose, and MAP) between groups were compared by a one-way analysis of variance (ANOVA). All values were reported as means±standard deviation unless otherwise stated. A one-way analysis of variance (ANOVA) was used to determine the between-group differences in latency time for finding the platform during the MWM on day 14. When an overall significant difference was found, a Tukey post-hoc analysis was used to determine specific between-group differences. Performances on the MWM (learning curve) between days 10 and 14 were compared between groups by a repeated measure ANOVA. Neurological deficit scores between groups were assessed by Kruskal-Wallis analysis. For all analyses, alpha was set at a p<0.05 level of significance.

IV. Results

Physiological variables, including arterial blood gas (ABG), glucose, and MAP were similar between groups at baseline. Time to cardiac arrest (190±20 seconds) and duration of CPR (30±16 seconds) were similar between groups. Seven out of eight rats in each group had ROSC and survived 14 days. There were no significant differences in ABGs, glucose levels, and MAPs at 10, 30, 60, 90 and 120 minutes after ROSC between groups. However, the MAP dropped to 80 mm±10 mm Hg five minutes after NT69L administration (15 minutes after ROSC), while the control group MAP was 130±23 mm Hg (p<0.05, ANOVA). The MAP in the NT69L group returned to control values by 20 minutes after ROSC.

Figure 2:
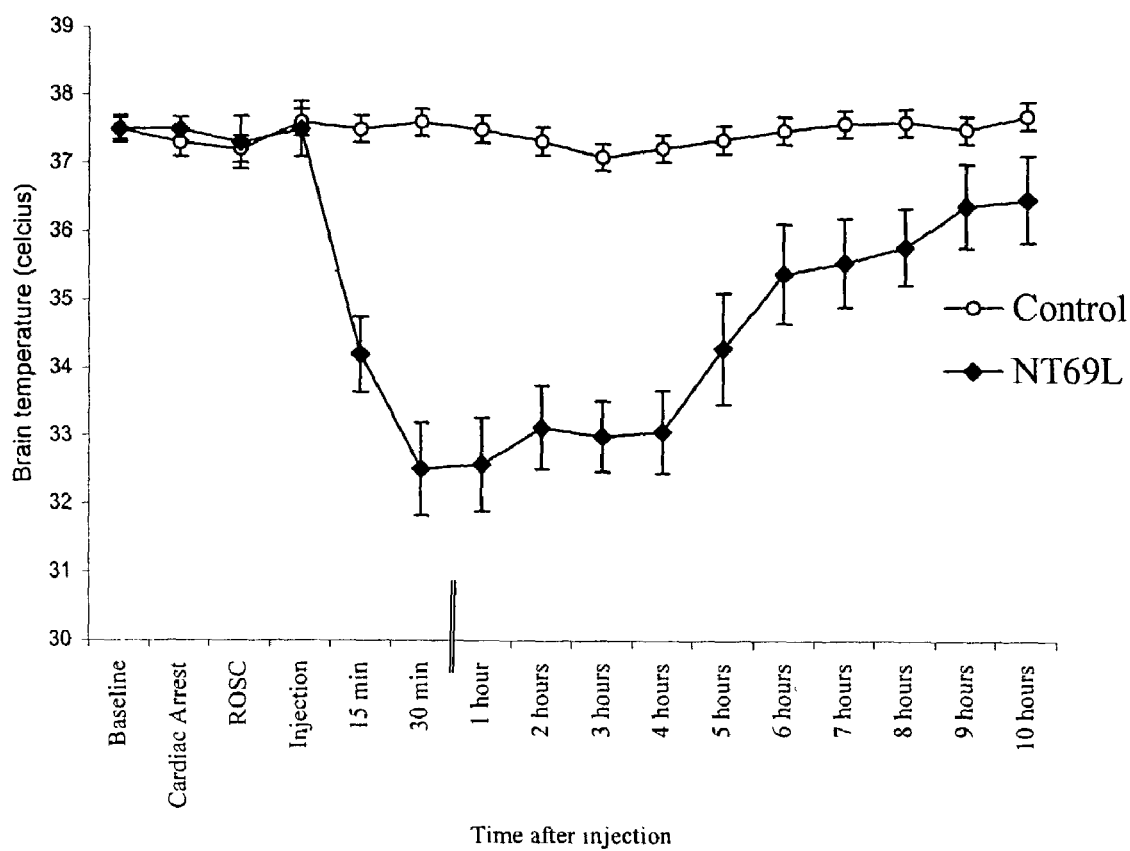
FIG. 2 is a comparison of brain temperature between control group rats (circle) and NT69L group rats (diamond) beginning at a baseline before cardiac arrest and extending to 10 hours after injection of saline or NT69L (see Example 1 below).

FIG. 2 shows a comparison of brain temperature in control group rats and NT69L group rats beginning at a baseline before cardiac arrest and extending to 10 hours after injection of saline or NT69L. Brain temperature dropped below 35° C. 13+3 minutes (range 8-15 minutes) after NT69L administration to rats while brain temperature in control rats remained 37.5±0.5° C. Mild hypothermia was maintained for 300±100 minutes (range 20-400, median 367 minutes) in the NT69L group, while the control rats maintained a brain temperature of 37.1±0.6° C. throughout 72 hours of monitoring after ROSC. The control group (30±10) had a significantly worse NDS compared with the NT69L group (3±3) ($p<0.05$, ANOVA).

Figure 3:
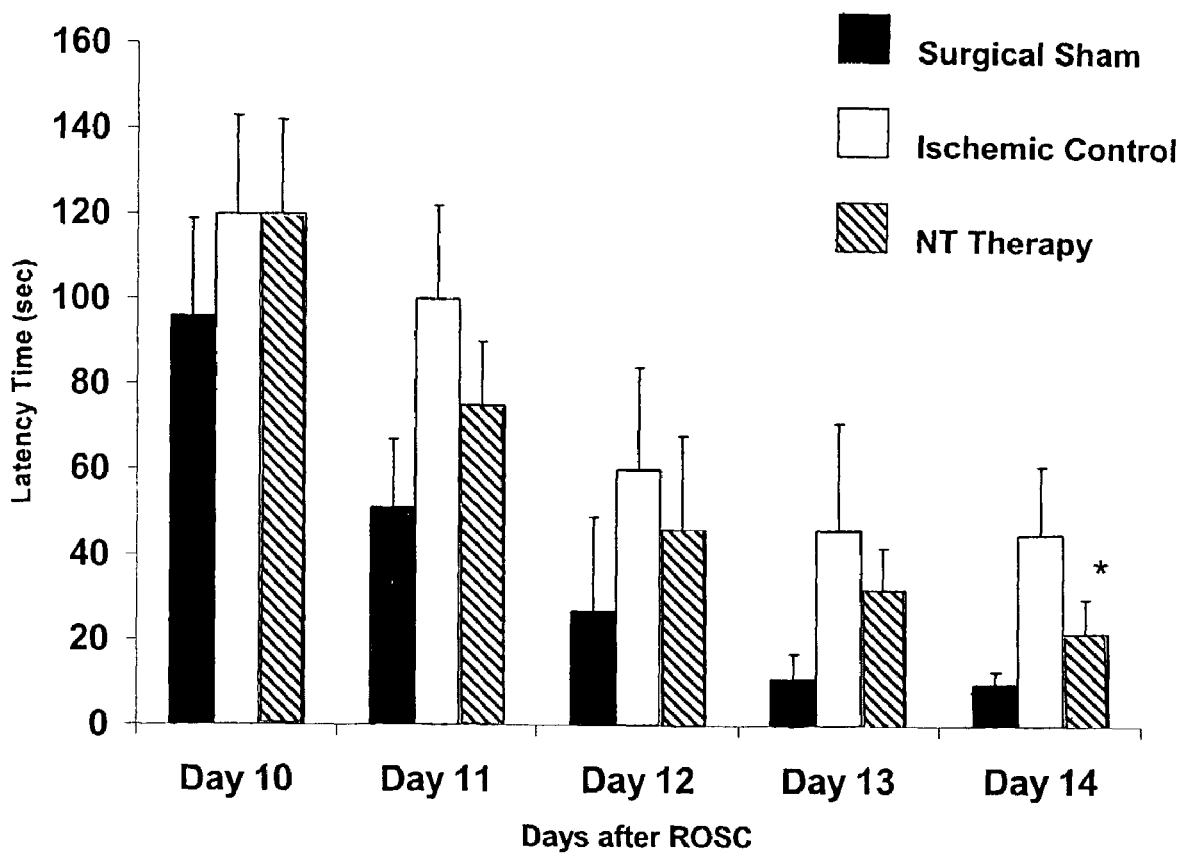
FIG. 3 shows a comparison of performance (i.e., latency time) in a Morris Water Maze on days 10-14 after resuscitation from asphyxial cardiac arrest for rats in a surgical sham group, an ischemic control group, and a NT69L therapy group (see Example 1 below).

FIG. 3 shows a comparison of performance (i.e., latency time) in a Morris Water Maze on days 10-14 after resuscitation from asphyxial cardiac arrest for rats in the surgical sham group, ischemic control group, and NT69L therapy group. There was no difference in the swimming speed during MWM testing between the sham group (27±2 cm/sec), the control group (25±1 cm/sec), and the NT69L (26±1 cm/sec) group. Fourteen days after ROSC, the latency time in the control group (45±26 sec) was significantly longer (worse) than that of the NT69L group (22±8 sec) ($p<0.05$, ANOVA Tukey post hoc). The latency time of the controls was also longer than that of the sham (10±3 sec) ($p<0.05$, ANOVA Tukey post hoc) (FIG. 3). There was no difference between the control and NT69L rats when comparing the rates of change of latency time over days 10-14 ($p=0.15$ repeated-measures ANOVA). However there was a more rapid decrease in latency time (increased learning) on days 10-14, when comparing sham rats with control and NT69L rats sustaining cardiac arrest and resuscitation ($p<0.05$, repeated-measures ANOVA).

Figure 4:
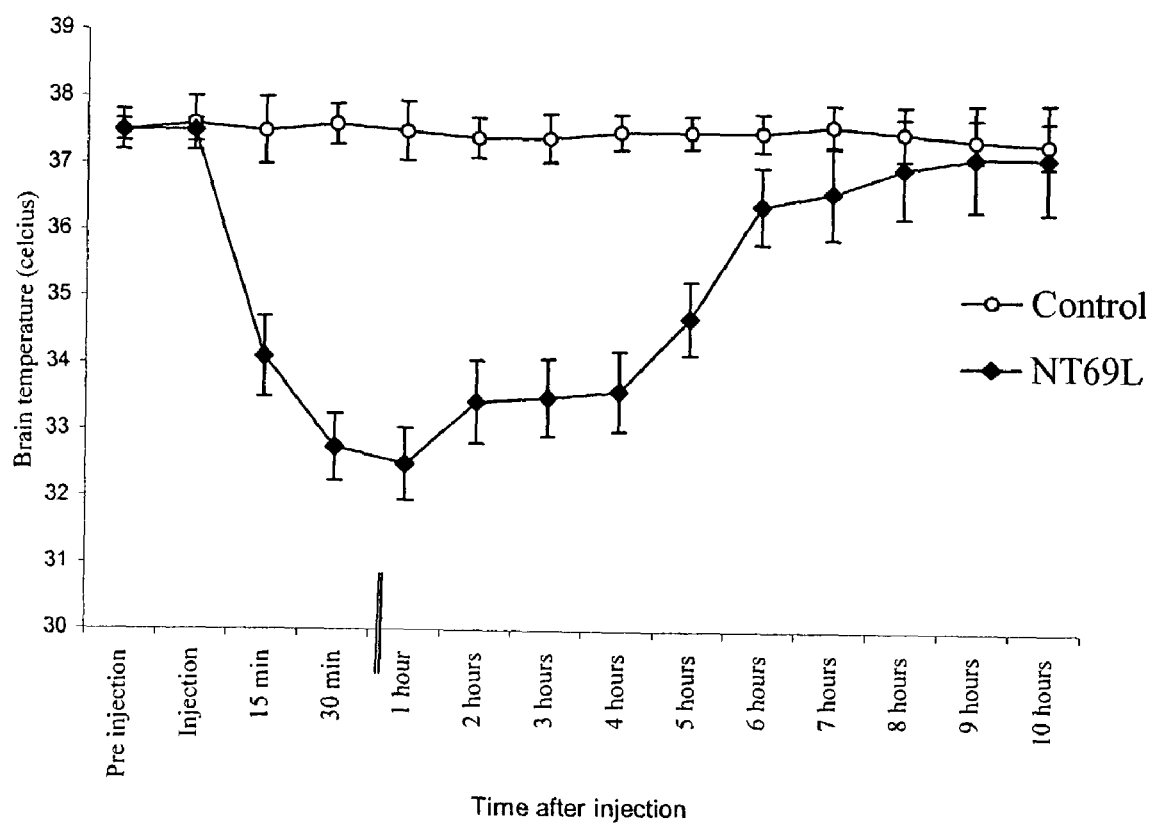
FIG. 4 shows a comparison of brain temperature between rats given normal saline (circle) and NT69L (diamond) without cardiac arrest and reperfusion before and after injection (see Example 1 below).

FIG. 4 shows a comparison of brain temperature between the control rats given normal saline and the rats given NT69L without cardiac arrest and reperfusion before and after injection. There was a drop in brain temperature in unanesthetized, free-roaming rats given NT69L when compared with that for control rats given saline in the same environment.

V. Discussion/Conclusion

The neurotensin analog NT69L administered intravenously after resuscitation from cardiac arrest produced rapid and prolonged mild hypothermia and improved neurological outcome.

The neurotensin analog NT69L was able to reduce latency time on the final day of performance in the MWM, but there was no statistically significant difference in the "learning curve" over days 10-14 when NT69L-treated rats were compared with control rats. The lack of difference between groups may have been due to the relatively mild cerebral insult, since both ischemic groups showed an ability to acquire new knowledge. In addition, the secondary cerebral ischemia (i.e., the transient hypotension) produced by the neurotensin analog may have negated some of the cerebral benefit of the neurotensin analog, as hypotension after cardiac arrest has been associated with a worse neurological outcome (see, e.g., Bleyaert et al., Effect of postcirculatory-arrest life-support on neurological recovery in monkeys, Critical Care Medicine, 8(3):153-6, 1980). However, the hypotension produced by NT69L is mild and transient and requires no therapeutic interventions for resolution. Although no histological data was taken to confirm that the neurotensin analog NT69L reduced structural brain damage when administered after resuscitation from asphyxial cardiac arrest, previous studies with this rat model have shown a correlation between NDS and histological damage (see, e.g., Katz et al., Outcome model of asphyxial cardiac arrest in rats, J. Cereb. Blood Flow Metab., 1995, 15:1032-1039). In addition, the improvement in performance on the MWM has also been correlated with decreased histological damage in this rat model (see, e.g., Hickey et al., Use of the Morris water maze and acoustic startle chamber to evaluate neurologic injury after asphyxial arrest in rats. Ped. Res. 1996, 39:77-84).

Example 2

Neurotensin Analog NT77 Induces Regulated Hypothermia

The purpose of this experiment was to determine whether the hypothermic response elicited by NT77 (a neurotensin analog that crosses the blood brain barrier and induces hyphernia) is mediated via a regulated mechanism (i.e., via reduction in set-point) or by a forced mechanism. During regulated hypothermia, there is little or no increase in metabolic rate or reduction in heat loss (e.g., peripheral vasoconstriction) that occur when the hypothermia is forced (see, e.g., Gordon, C. J., A review of terms and proposed nomenclature for regulated vs. forced changes in body temperature, Life Sciences 32, 1285-1295, 1983 and Gordon, C. J., Temperature Regulation in Laboratory Rodents, New York:Cambridge University Press, 1993), and a regulated hypothermic response is characterized by a behavioral thermoregulatory response to seek cold temperatures concomitant with a decrease in core temperature. Therefore, the hypothermic mechanism of NT77 was determined by assessing the effects of the NT77 on core temperature and selected ambient temperature of rats housed in a temperature gradient.

I. Animal Subjects and Preparation

Male rats of the Sprague-Dawley strain at 60 days of age were obtained from Charles River Laboratories (Raleigh, N.C.). The animals were housed individually in acrylic cages lined with wood shavings at an ambient temperature ($T_a$) of 22° C., relative humidity of 50%, and a 12 hour light:12 hour dark photoperiod (lights were turned on at 6 a.m. and turned off at 6 p.m.).

Core temperature and motor activity were monitored in undisturbed rats using radio telemetry (Data Sciences International, St. Paul, Minn.). Details of the telemetry system are described in Gordon, C. J., 24-hour control of body temperature in the rat: I. Integration of behavioral and autonomic effectors, Am. J. Physiol. 267, R71-R77, 1994. Briefly, rats were anesthetized with sodium pentobarbital (50 mg/kg; intraperitoneally) and an incision was made for the implantation of the transmitter (TAIOTA-F40) into the abdominal cavity. The abdominal muscle was sutured and the skin was closed with wound clips. Following surgery, rats were administered a penicillin antibiotic (30,000 units; intramuscularly) and analgesic (buprenorphine; 0.03 mg/kg; subcutaneously). The rats were allowed at least 10 days of recovery before testing.

II. Procedures

A. Behavioral Thermoregulation

The behavioral thermoregulatory response to NT77 was assessed by measuring selected ambient temperature (Selected $T_a$) of the unrestrained rats when housed in a temperature gradient (Gordon, C. J., 24-hour control of body temperature in the rat: I. Integration of behavioral and autonomic effectors, Am. J. Physiol. 267, R71-R77, 1994).

Rats were placed in a temperature gradient and allowed to behaviorally select from a range of ambient temperatures ($T_a$) while core temperature ($T_c$) was monitored by radiotelemetry. Selected $T_a$, core temperature ($T_c$), and motor activity were monitored at 1 minute intervals. The gradient consisted of a wire-mesh cage placed inside a copper tube heated at one end and cooled at the other end with recirculating water baths. The range of ambient temperatures in the gradient varied from 15° C. to 38° C. The rat could move about in the 2 m-long gradient and select along a near linear change in $T_a$. Selected $T_a$ was measured by photocells positioned at 10 cm intervals that detected the position of the rat in the gradient and automatically compared the position to the air temperature measured by thermocouples placed immediately outside the wire-mesh cage. Motor activity was calculated by measuring the change in position of the rat in the gradient at 1 minute intervals. Food and water were provided ad libitum in the middle of the gradient. Air was continually circulated through the gradient and a strip of low voltage lights illuminated the interior of the gradient on a 12 hour light:12 hour dark photoperiod set at the same time as that of the animal facility.

A naive rat was placed in the gradient in the afternoon of the day before injection and was allowed to adapt overnight to the gradient prior to testing. The following day the rat was removed from the gradient at 10 AM and injected intraperitoneally with saline or with 5.0 mg/kg NT77 (0.1 ml/100 g body weight). The rat was immediately placed back in the middle of the gradient and left undisturbed until the next morning. The rat was out of the gradient for as little time as possible and injection required less than 1.0 minute. The behavioral and core temperature data were recorded at 1 minute intervals throughout the experiment. Mean body weight of the rats when placed in the gradient was 489 g.

B. Metabolism and Heat Loss

Oxygen consumption and dry heat loss were measured in naive rats implanted with radiotransmitters and housed in a direct calorimeter. The internal dimensions of the calorimeter were 30.5 cm×30.5 cm×30.5 cm. The calorimeter was used to measure the rate of dry heat loss (i.e., thermal conductance) from the rats using thermoelectric sensors in the calorimeter walls. The calorimeter was housed inside a temperature-controlled chamber maintained at 23.5° C. The inside of the calorimeter was dimly illuminated with LED lights (total power=0.2 Watts).

The rats were housed in a wire-mesh cage that was placed in a metal pan that had a thin layer of mineral oil to collect urine and prevent moisture from interfering with the measurement of evaporative water loss. A wire mesh lid was placed over the cage and two telemetry receiver wands (Data Sciences, model RLA 3000) were placed over the top of the cage to detect the telemetry signal.

A mass flow controller was used to meter dry air at a constant flow rate (2.7 liters/minute; STP) into the calorimeter. A fraction of the air leaving the chamber was dried and passed through an oxygen analyzer (Applied Electrochemistry) to measure the percent oxygen. Metabolic rate of the rat was estimated by measuring the oxygen consumption. The change in percent oxygen before and after passing through the calorimeter was multiplied by the flow rate of air into the chamber to calculate metabolic rate in dimensions of ml $O_2$/(min kg). The calorimeter was calibrated by burning a small lamp alcohol lamp containing 100% ethanol inside the calorimeter for several hours. The change in weight of the lamp was used to determine the expected rate of oxygen consumption assuming complete and steady combustion of the ethanol. The rate of dry heat loss in the calorimeter was calibrated with a precision resistor that was heated to a specific voltage with a calibrated power source. Percent oxygen, dry heat loss, air flow rate, and calorimeter temperature were monitored at 1 minute intervals by a data acquisition system (Dianachart PC acquisitor). Dry thermal conductance in dimensions of Watts/° C. (W/C) was calculated by dividing the value of dry heat loss at 1 minute intervals by the difference between core and ambient temperature. Thermal conductance is a measure of facility of heat transfer (i.e., heat loss) from the rat and provides information on the peripheral vasomotor state of the animal (Gordon, C. J., Temperature Regulation in Laboratory Rodents, New York:Cambridge University Press, 1993).

A naive rat was placed in the wire-mesh cage which was then placed inside the calorimeter at approximately 9 a.m. The rat was allowed to acclimate to the calorimeter for 115 minutes. Due to drift of the signal of the oxygen analyzer it was necessary to periodically monitor the percent oxygen of the inflowing air. Hence, just prior to dosing, the air flow to the oxygen analyzer was switched so that the percent oxygen of the inflowing air could be measured. At 120 minutes after placement in the calorimeter, the rat was quickly removed from the system and injected intraperitoneally with either sterile saline or 5.0 mg/kg NT77. The rat was quickly placed back into the chamber and the door sealed. At this time, the percent oxygen of air leaving the calorimeter was shunted to the oxygen analyzer. After 115 minutes, the percent oxygen of the inflowing air was measured for another 5 minutes for calibration purposes but the rat was not disturbed. After another 115 minutes, the rat was removed from the calorimeter and weighed. The mean weight between entering and leaving the calorimeter was used in the calculation of metabolic rate.

III. Data Analysis

For statistical analysis, the core temperature and selected $T_a$ data from the behavioral studies were averaged into thirty bins. These data were subjected to a two-way repeated measures analysis of variance (ANOVA) to assess effect of treatment (saline vs. NT77) and time on each recorded parameter. Significant interactions with $p<0.05$ were followed with a Tukey's test to assess significance at specific time points. The core temperature, oxygen consumption, and heat loss data were analyzed at selected time intervals following injection of saline and NT77 with repeated measures ANOVA.

IV. Results

A. Behavioral Thermoregulation

When first placed in the temperature gradient, the rats generally selected relatively 0.17 cool $T_a$'s and maintained an elevated core temperature for several hours. By the next day, rats displayed a selected $T_a$ of approximately 28° C. and core temperature of 37.5° C.

Figure 5A:
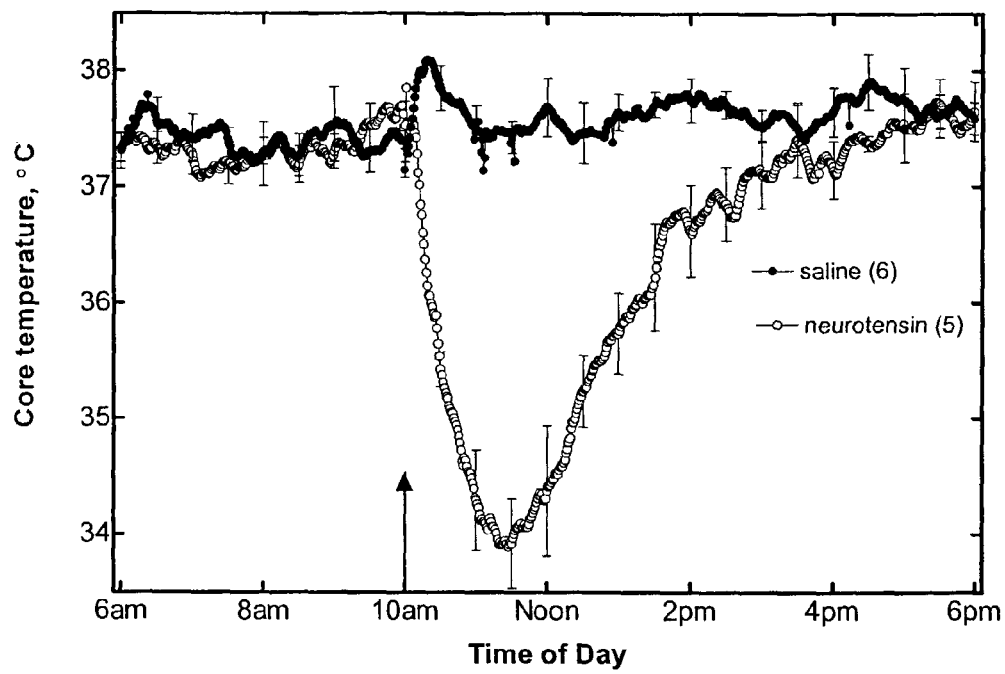
FIGS. 5A-5C illustrate time-course of mean and standard error of core temperature (FIG. 5A), selected ambient temperature ($T_a$) (FIG. 5B), and motor activity (FIG. 5C) of rats dosed intraperitoneally with saline or 5.0 mg/kg NT77 before and after the injection (see Example 2 below). The core temperature is plotted each minute whereas selected $T_a$ is averaged over 30 minute intervals. Error bars for core temperature are shown for each 30 minutes. Numbers in parentheses indicate sample size.
Figure 5B:
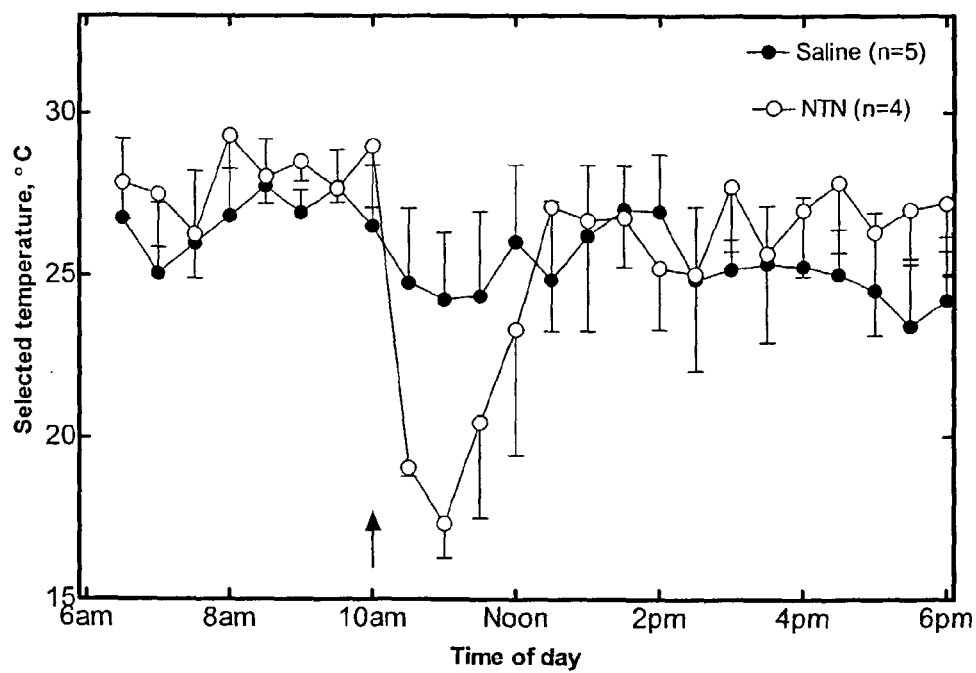

FIGS. 5A and 5B illustrate the time-course of mean and standard error of core temperature and selected ambient temperature, respectively, of rats dosed intraperitoneally with saline or 5.0 mg/kg NT77 both before and after injection. Following injection of saline, there was a transient reduction in selected $T_a$ and elevation in core temperature that persisted for approximately 1 hour, which is a typical response to the stress of handling and injection. Administration of 5.0 mg/kg NT77 resulted in a simultaneous reduction in selected $T_a$ and core temperature. Within 30 minutes after injection of NT77, mean selected $T_a$ had decreased from 29° C. to 19° C. while core temperature decreased from 37.5° C. to 34° C. Selected $T_a$ reached a nadir of 16° C. by one hour after injection and then slowly recovered to control levels over the next 90 minutes. Core temperature reached a nadir of 34° C. by 90 minutes after injection and recovered to control levels over the next 4 hours.

Figure 5C:
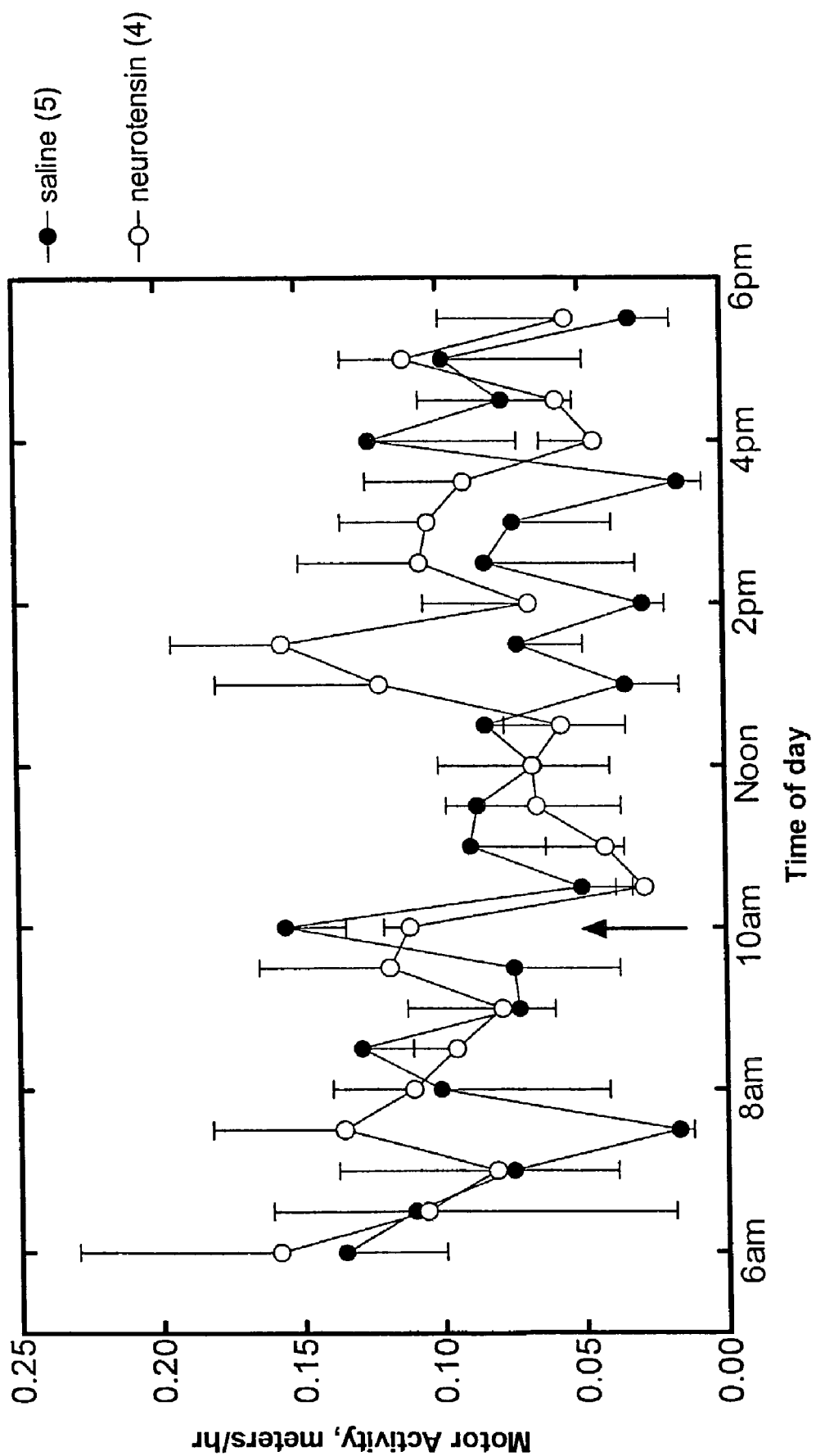

FIG. 5C illustrates the time-course of mean and standard error of motor activity of rats dosed IP with saline or 5.0 mg/kg NT77. There was a transient increase in motor activity following injection of saline and NT77. Overall, NT77 had no effect on motor activity of rats housed in the temperature gradient.

Figure 6A:
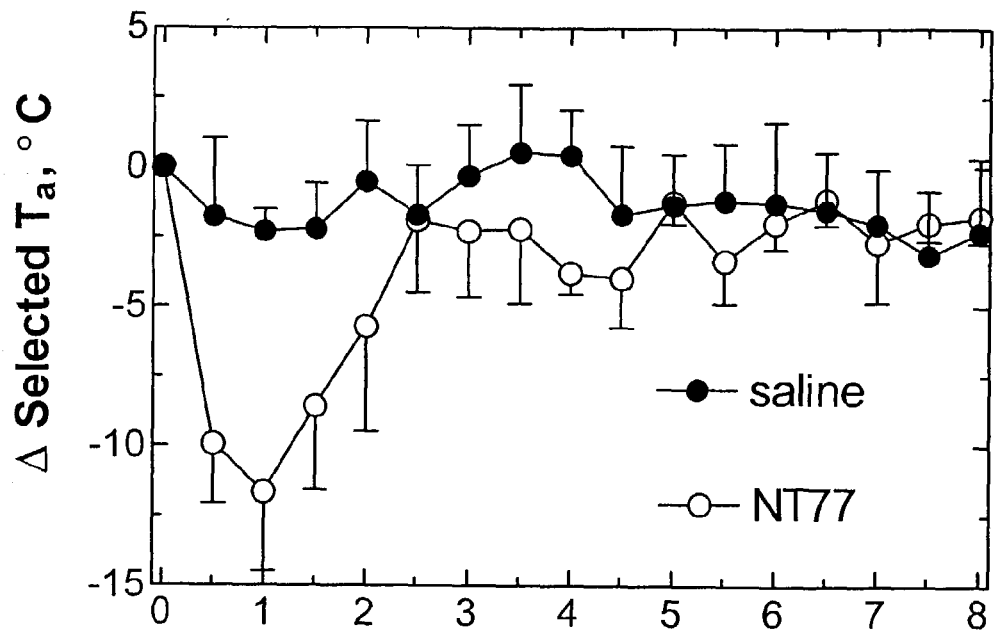
FIGS. 6A and 6B illustrate the change in selected ambient temperature ($T_a$) (i.e., Δ selected $T_a$) (FIG. 6A) and core temperature (i.e., Δ core temperature) (FIG. 6B) relative to the values measured prior to NT77 or saline injection. Sample sizes for FIG. 6A were the same as in FIG. 5B. Sample sizes for FIG. 6B were the same as in FIG. 5A.
Figure 6B:
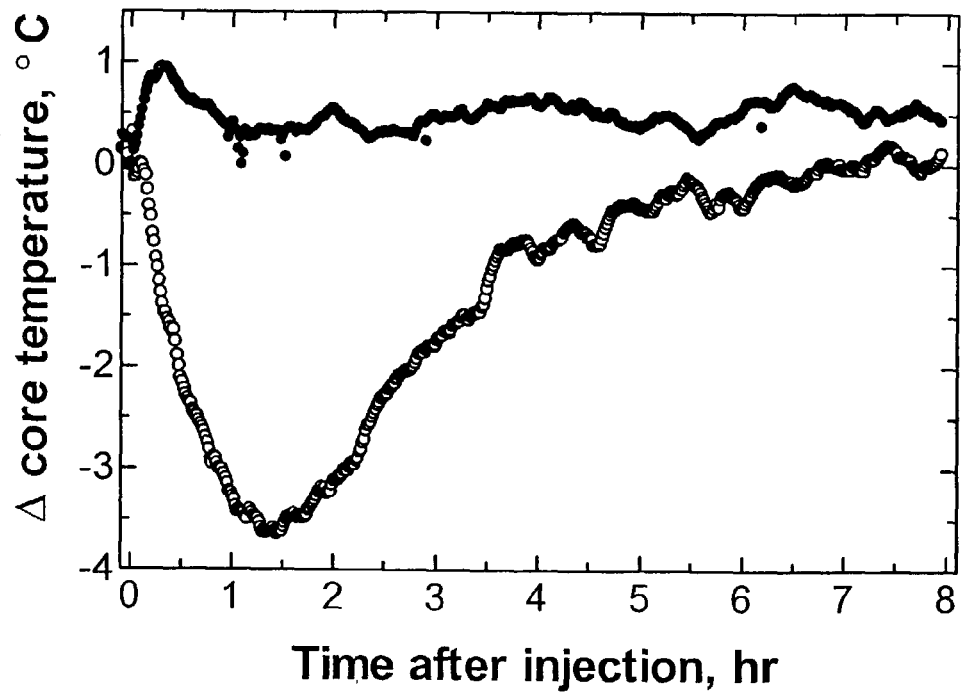

FIGS. 6A and 6B illustrate the change in selected $T_a$ (i.e., $\Delta$ selected $T_a$) and core temperature (i.e., $\Delta$ core temperature), respectively, relative to the values measured prior to NT77 or saline injection. The change in core temperature and selected $T_a$ relative to the values measured prior to dosing shows the preference for cooler $T_a$'s that precedes the nadir of the decrease in core temperature. By 1.5 hours after injection of NT77, core temperature reached a 3.5° C. nadir while selected $T_a$ has initiated a slight recovery. It is important to note that the rats remained hypothermic for 6 hr after NT77 while selected $T_a$ remained at control levels. The rats did not select significantly warmer $T_a$'s for any length of time that would accelerate the rate of warming and reduce the period of hypothermia.

Figure 7:
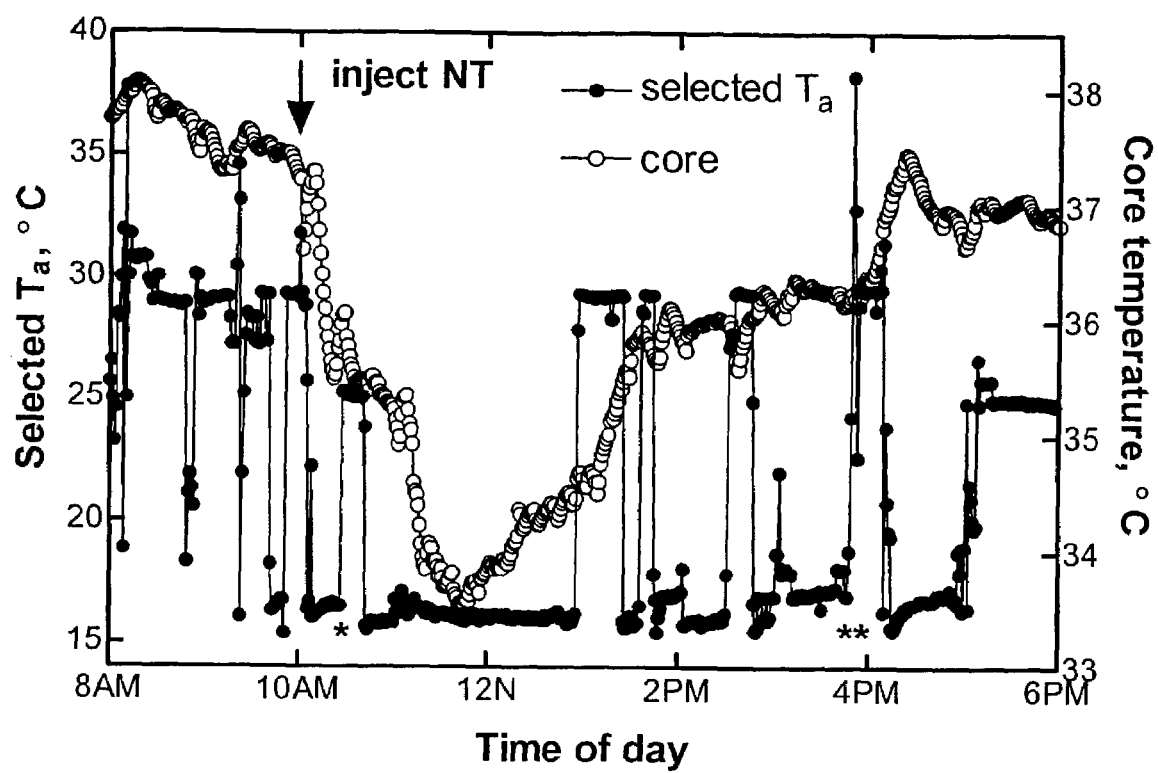
FIG. 7 illustrates a minute-to-minute plot of selected ambient temperature ($T_a$) and core temperature of one rat administered 5.0 mg/kg NT77 both before and after injection. As described in Example 2 below, asterisks (i.e., *.

FIG. 7 illustrates a minute-to-minute plot of selected $T_a$ and core temperature of one rat administered 5.0 mg/kg NT77 both before and after injection. The minute-to-minute plot shows the dynamic changes in behavioral thermoregulation that cannot be seen with a plot using the thirty minute averaging of the data. As shown in FIG. 7, there is an abrupt preference for cold $T_a$'s within a couple of minutes after dosing that is then followed by a fall in core temperature. That is, the behavioral response to NT77 preceded the change in core temperature. There were transient changes in selected $T_a$ preceding the changes in core temperature after NT77 injection (see portions of FIG. 7 marked with an asterisk symbol (i.e., "*" or "**"). In the part marked with one asterisk (i.e., "*"), the, rat moved to warmer temperatures for 4 minutes. This led to a transient rise in core temperature but the rat then moved to the coldest part of the gradient for the next hour and core temperature fell dramatically. In the part marked with two asterisks (i.e., "**"), the rat moved to the warmest part of the gradient for 1 minute then settled at 28° C. for several minutes. Core temperature increased for several minutes and the rat then went to the coldest side of the gradient for the next 30 minutes and core temperature fell again. It was also noted that prior to NT77 injection, the spontaneous changes in selected $T_a$ had little effect on core temperature.

The rats treated with NT77 displayed normal core temperatures and selected $T_a$'s during the night after treatment (data not shown). Body weight measured the day after treatment was similar for saline and NT77 treated animals. Rats dosed with saline and NT77 lost 1.6% and 2.4% of their initial body weight, respectively.

B. Metabolism and Heat Loss

When rats were first placed in the calorimeter their oxygen consumption (M) and heat loss (H) increased transiently for approximately 1 hr and then decreased to steady state levels. When the chamber was opened to inject the rat, the influx of ambient air into the calorimeter resulted in an artifactual reduction in oxygen consumption. FIGS. 8A and 8B illustrate the relative change in oxygen consumption and heat loss, respectively, of rats dosed with saline or NT77., The relative changes in these parameters were calculated based on the average of the measured values of oxygen consumption and heat loss over the 15 minute period immediately prior to NT77 and saline injection. Rats dosed with saline underwent a transient increase in core temperature and oxygen consumption. Thus, the rise in oxygen consumption required several minutes to observe as the sealed calorimeter reached equilibrium. Heat loss was initially unchanged after saline but then increased sharply at a time coinciding with the peak elevation in core temperature. Rats dosed with NT77 underwent a marked reduction in core temperature, decreasing an average of 3° C. over a 1 hour period after dosing. The hypothermic response to NT77 was associated with a reduction in oxygen consumption and relatively little change in heat loss for the first 20 minutes after dosing. After this time, heat loss began to slowly decrease steadily over the next 2 hours. Oxygen consumption at 30 minutes after NT77 was 30% below that of the rats dosed with saline; by 1 hour after injection, oxygen consumption of the NT rats was a steady 20% below that of the rats dosed with saline. Motor activity in the calorimeter increased transiently after injection of saline and NT77. However, as in the temperature gradient, there was no discernable effect of the NT77 injection on motor activity (data not shown).

FIGS. 9A and 9B illustrate the relationship between core temperature and dry thermal conductance, respectively, of rats housed in calorimeter and injected with saline or NT77. Thermal conductance is a measure of the rate of heat transfer from the rat to the calorimeter. The dry thermal conductance reveals the changes in peripheral vasomotor tone after injection of saline and NT77. In this example, thermal conductance displayed a steady elevation for approximately 1 hour after injection of NT77. As core temperature reached its nadir, thermal conductance began a slow decrease. This can be interpreted as an increase in skin blood flow during the period when core temperature is decreasing. Thermal conductance of rats dosed with saline is also of interest because conductance decreased transiently after injection of saline, concomitant with a sharp increase in core temperature, which suggests a transient reduction in heat loss following the stress of handling and injection of saline. After the peak hyperthermic response, there was a transient increase in conductance which represents a heat dissipatory response.

Thermal conductance remained unchanged in rats dosed with saline for approximately 10 minutes after dosing then increased sharply at a time when core temperature reached the peak after saline. Thermal conductance of rats dosed with NT77 increased immediately after dosing and remained above control levels for nearly 2 hours after dosing. Thermal conductance then decreased below control levels over the last 2 hours of testing and is associated with the time when core temperature was starting to recover to control levels.

V. Conclusion

The results of this study show that systemic administration of the neurotensin analog NT77 elicited a regulated hypothermic response in the rat. This conclusion is warranted by the fact that the rats immediately selected cold $T_a$ following NT77 injection and this behavioral response is followed by a reduction in core temperature. Moreover, rats injected with NT77 underwent a rapid decrease in oxygen consumption and little change in heat loss as core temperature began to decrease. If NT77 induced a forced hypothermic response, then the rats would be expected to have a preference for warmer $T_a$'s. Also, if NT77's effect was limited to behavioral thermoregulation without affecting core temperature, then a preference for a colder $T_a$ alone would not be expected to result in hypothermia. That is, an unanesthetized rat could easily maintain its core temperature against the cold stress encountered at the coldest end of the gradient (see, e.g., Gordon, C. J., Temperature Regulation in Laboratory Rodents, New York:Cambridge University Press, 1993). Therefore, NT77 activates a coordinated thermoregulatory response that leads to a reduction in set-point temperature, a preference for cooler ambient temperatures, and a lowering of core temperature.

Example 3

Treatment of Hypoxic Ischemia Caused by Asphyxial Cardiac Arrest Using Neurotensin Analog NT77

The purpose of the experiment was (1) to determine whether NT77 could reduce brain damage due to reperfusion injury after cerebral ischemia caused by asphyxial cardiac arrest and (2) to determine whether regulated hypothermia induced by NT77 after reperfusion from asphyxial cardiac arrest would alter malondialdehyde (MDA) levels in the brain during reperfusion.

This experiment was performed using materials and methods similar to those described in Example 1. The outcome model of asphyxial cardiac arrest in rats described in Example 1 was used to induce the cerebral insult in all rats. However, instead of NT69L being used as the neurotensin analog, NT77 was used. Also, in addition to a control group (saline), a treatment/regulated hypothermia group (NT77), and a surgical sham group (no asphyxial cardiac arrest), two additional test groups were added. A forced brief hypothermia group and a forced prolonged hypothermia group were also used in the experiment. The rats in the forced brief hypothermia group and the forced prolonged hypothermia group were subjected to conventional conductive cooling using ice beginning at 30 minutes following ROSC to induce mild hypothermia. Cooling was continued in the forced brief hypothermia group until 4 hours following ROSC. Cooling was continued in the forced prolonged hypothermia group until 24 hours following ROSC. A time course of the brain temperature in each group beginning at a baseline before cardiac arrest and extending to 48 hours after ROSC is shown in FIG. 12. Thirty minutes after ROSC, NT77 (10 mg/kg) was injected in the regulated hypothermia group and a similar volume of saline was injected in the control group.

FIG. 10 illustrates a comparison of neurological deficit scores at 72 hours after asphyxial cardiac arrest in the control, forced brief hypothermia, forced prolonged hypothermia, and regulated hypothermia (NT77) groups. FIG. 11 shows a comparison of performance (i.e., latency time) in a Morris Water Maze on days 10-14 after asphyxial cardiac arrest for rats in a surgical sham group, a control group, a forced brief hypothermia group, a forced prolonged hypothermia group, and a NT77 group. The results show that inducing regulated hypothermia using NT77 after cerebral ischemia caused by asphyxial cardiac arrest improved neurological outcome of rats dosed with NT77.

In addition to the above mentioned measurements, the level of malondialdehyde in the hippocampus of the rats in the control (saline), forced brief hypothermia, forced prolonged hypothermia, and regulated hypothermia (NT77) groups was measured at various time points before and after asphyxial cardiac arrest. Malondialdehyde levels are believed to be an indicator of oxidative stress (e.g., free radicals/lipid peroxidation) in the brain due to reperfusion injury. FIG. 13 illustrates the levels of (MDA) in the hippocampus of rats in control, forced brief hypothermia, forced prolonged hypothermia, and regulated hypothermia (NT77) groups before and after asphyxial cardiac arrest (ACA) at the indicated time points. The results are shown as means and standard deviations in micromoles/gram brain tissue. At 24 hours after asphyxial cardiac arrest, the levels of MDA present in the hippocampus of rats treated with NT77 was markedly lower than the control group and forced brief hypothermia groups. The results indicate that the NT77 was effective in reducing the levels of MDA in the brain during reperfusion.

While the invention has been described in detail and with reference to specific embodiments thereof, it will be apparent to one skilled in the art that various changes and modifications can be made without departing from the spirit and scope of the invention.

What is claimed is:

1. A method of treating cerebral ischemia in a mammal, the method comprising inducing hypothermia in a mammal during, or following cerebral ischemia in the mammal by administering to the mammal about 0.5 mg/kg to 10 mg/kg of a neurotensin analog capable of crossing the blood-brain barrier, wherein the neurotensin analog is selected from the group consisting of NT69L and NT77.

2. The method of claim 1 wherein the cerebral ischemia is global cerebral ischemia.

3. The method of claim 1 wherein the cerebral ischemia is focal cerebral ischemia.

4. The method of claim 1 wherein the cerebral ischemia is due to cardiac arrest, traumatic brain injury, stroke, near drowning, birth asphyxia, or drug overdose.

5. The method of claim 1 wherein the mammal is human.

6. The method of claim 1 wherein the neurotensin analog is administered after onset of cerebral ischemia in the mammal.

7. The method of claim 6 wherein the neurotensin analog is administered after onset of reperfusion in the mammal.

8. The method of claim 2 wherein the global cerebral ischemia is due to cardiac arrest.

9. The method of claim 3 wherein the focal cerebral ischemia is due to stroke.

10. A method of treating cerebral ischemia in a mammal, the method comprising inducing regulated hypothermia in a mammal during, or following cerebral ischemia in the mammal by administering to the mammal about 0.5 mg/kg to 10 mg/kg of a neurotensin analog capable of crossing the blood-brain barrier, wherein the neurotensin analog is selected from the group consisting of NT69L and NT77.

11. The method of claim 10 wherein the cerebral ischemia is global cerebral ischemia.

12. The method of claim 10 wherein the cerebral ischemia is focal cerebral ischemia.

13. The method of claim 10 wherein the cerebral ischemia is due to cardiac arrest, traumatic brain injury, stroke, near drowning, birth asphyxia, or drug overdose.

14. The method of claim 10 wherein the mammal is human.

15. The method of claim 10 wherein the neurotensin analog is administered after onset of cerebral ischemia in the mammal.

16. The method of claim 15 wherein the neurotensin analog is administered after onset of reperfusion in the mammal.

17. The method of claim 11 wherein the global cerebral ischemia is due to cardiac arrest.

18. The method of claim 12 wherein the focal cerebral ischemia is due to stroke.

19. A method of treating global cerebral ischemia in a mammal, the method comprising inducing regulated hypothermia in a mammal during or following global cerebral ischemia in the mammal by administering to the mammal an effective dose of a neurotensin analog selected from the group consisting of NT69L and NT77.

20. The method of claim 19 wherein the global cerebral ischemia is due to cardiac arrest.

21. The method of claim 20 wherein the neurotensin analog is administered after onset of reperfusion in the mammal.

22. The method of claim 21 wherein the mammal is a human.

23. A method of treating focal cerebral ischemia in a mammal, the method comprising inducing regulated hypo thermia in a mammal during or following focal cerebral ischemia in the mammal by administering to the mammal an effective dose of a neurotensin analog selected from the group consisting of NT69L and NT77.

24. The method of claim 23 wherein the focal cerebral ischemia is due to stroke.

25. The method of claim 24 wherein the neurotensin analog is administered after onset of reperfusion in the mammal.

26. The method of claim 25 wherein the mammal is a human.

* * * * *

UNITED STATES PATENT AND TRADEMARK OFFICE
CERTIFICATE OF CORRECTION

| | | |
|---|---|---|
| PATENT NO. | : 7,319,090 B2 | |
| APPLICATION NO. | : 10/306672 | |
| DATED | : January 15, 2008 | |
| INVENTOR(S) | : Lawrence M. Katz | |

It is certified that error appears in the above-identified patent and that said Letters Patent is hereby corrected as shown below:

<u>Column 7,</u>

<u>Line 1</u>: should read:

--Example 2 of the patent (i.e., "Neurotensin Receptor Binding Properties of neo-tryptophan-containing polypeptides") states that a plot of $K_d$ (i.e., equilibrium dissociation constant) values obtained using a human neurotensin receptor for various NT analogs against the respective $K_d$ values of a rat neurotensin receptor revealed a strong correlation between the binding affinity of various neurotensin analogs at the human and rat neurotensin receptors.--

Signed and Sealed this

Third Day of June, 2008

JON W. DUDAS
*Director of the United States Patent and Trademark Office*

SEQUENCE LISTING

```
<160> NUMBER OF SEQ ID NOS: 30

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: p-Glu

<400> SEQUENCE: 1

Glu Leu Tyr Glu Asn Lys Pro Arg Arg Pro Tyr Ile Leu
 1               5                  10

<210> SEQ ID NO 2
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 2

Arg Arg Pro Tyr Ile Leu
  1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Pro Tyr Ile Leu
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Pro Trp Ile Leu
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: tert-Leu

<400> SEQUENCE: 5

Arg Arg Pro Tyr Leu Leu
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: N-methyl-Arg
<220> FEATURE:
<221> NAME/KEY: MOD_RES
<222> LOCATION: (5)
<223> OTHER INFORMATION: tert-Leu

<400> SEQUENCE: 6

Arg Lys Pro Trp Leu Leu
  1               5
```

```
<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Lys

<400> SEQUENCE: 7

Lys Arg Pro Tyr Ile Leu
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Orn

<400> SEQUENCE: 8

Arg Xaa Pro Tyr Ile Leu
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: L-3,1'-Nal

<400> SEQUENCE: 9

Arg Arg Pro Xaa Ile Leu
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: D-neo-Trp

<400> SEQUENCE: 10

Arg Arg Pro Trp Ile Leu
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)
<223> OTHER INFORMATION: neo-Trp

<400> SEQUENCE: 11

Arg Arg Pro Trp Ile Leu
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: neo-Trp
<220> FEATURE:
<221> NAME/KEY: MOD_RES
<222> LOCATION: (5)
<223> OTHER INFORMATION: tert-Leu

<400> SEQUENCE: 12

Arg Arg Pro Trp Leu Leu
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Lys
<220> FEATURE:
<221> NAME/KEY: MOD_RES
<222> LOCATION: (4)
<223> OTHER INFORMATION: D-neo-Trp
<220> FEATURE:
<221> NAME/KEY: MOD_RES
<222> LOCATION: (5)
<223> OTHER INFORMATION: tert-Leu

<400> SEQUENCE: 13

Lys Arg Pro Trp Leu Leu
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Lys
<220> FEATURE:
<221> NAME/KEY: MOD_RES
<222> LOCATION: (4)
<223> OTHER INFORMATION: neo-Trp
<220> FEATURE:
<221> NAME/KEY: MOD_RES
<222> LOCATION: (5)
<223> OTHER INFORMATION: tert-Leu
```

```
<400> SEQUENCE: 14

Lys Arg Pro Trp Leu Leu
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Lys
<220> FEATURE:
<221> NAME/KEY: MOD_RES
<222> LOCATION: (4)
<223> OTHER INFORMATION: neo-Trp

<400> SEQUENCE: 15

Lys Arg Pro Trp Ile Leu
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: N-methyl-Arg
<220> FEATURE:
<221> NAME/KEY: MOD_RES
<222> LOCATION: (4)
<223> OTHER INFORMATION: L-neo-Trp
<220> FEATURE:
<221> NAME/KEY: MOD_RES
<222> LOCATION: (5)
<223> OTHER INFORMATION: tert-Leu

<400> SEQUENCE: 16

Arg Lys Pro Trp Leu Leu
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: N-methyl-Arg
<220> FEATURE:
<221> NAME/KEY: MOD_RES
<222> LOCATION: (4)
<223> OTHER INFORMATION: neo-Trp
<220> FEATURE:
<221> NAME/KEY: MOD_RES
<222> LOCATION: (5)
<223> OTHER INFORMATION: tert-Leu

<400> SEQUENCE: 17

Arg Arg Pro Trp Leu Leu
 1               5
```

```
<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: N-methyl-Arg
<220> FEATURE:
<221> NAME/KEY: MOD_RES
<222> LOCATION: (2)
<223> OTHER INFORMATION: DAB
<220> FEATURE:
<221> NAME/KEY: MOD_RES
<222> LOCATION: (4)
<223> OTHER INFORMATION: neo-Trp
<220> FEATURE:
<221> NAME/KEY: MOD_RES
<222> LOCATION: (5)
<223> OTHER INFORMATION: tert-Leu

<400> SEQUENCE: 18

Arg Xaa Pro Trp Leu Leu
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Lys
<220> FEATURE:
<221> NAME/KEY: MOD_RES
<222> LOCATION: (3)
<223> OTHER INFORMATION: neo-Trp
<220> FEATURE:
<221> NAME/KEY: MOD_RES
<222> LOCATION: (4)
<223> OTHER INFORMATION: tert-Leu

<400> SEQUENCE: 19

Lys Pro Trp Leu Leu
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Lys
<220> FEATURE:
<221> NAME/KEY: MOD_RES
<222> LOCATION: (3)
<223> OTHER INFORMATION: neo-Trp

<400> SEQUENCE: 20

Lys Pro Trp Ile Leu
 1               5
```

```
<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: DAB
<220> FEATURE:
<221> NAME/KEY: MOD_RES
<222> LOCATION: (3)
<223> OTHER INFORMATION: neo-Trp
<220> FEATURE:
<221> NAME/KEY: MOD_RES
<222> LOCATION: (4)
<223> OTHER INFORMATION: tert-Leu

<400> SEQUENCE: 21

Xaa Pro Trp Leu Leu
 1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: DAB
<220> FEATURE:
<221> NAME/KEY: MOD_RES
<222> LOCATION: (3)
<223> OTHER INFORMATION: neo-Trp

<400> SEQUENCE: 22

Xaa Pro Trp Ile Leu
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Orn
<220> FEATURE:
<221> NAME/KEY: MOD_RES
<222> LOCATION: (4)
<223> OTHER INFORMATION: neo-Trp

<400> SEQUENCE: 23

Arg Xaa Pro Trp Ile Leu
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)
<223> OTHER INFORMATION: D-Orn
<220> FEATURE:
<221> NAME/KEY: MOD_RES
<222> LOCATION: (4)
<223> OTHER INFORMATION: neo-Trp
<220> FEATURE:
<221> NAME/KEY: MOD_RES
<222> LOCATION: (5)
<223> OTHER INFORMATION: tert-Leu

<400> SEQUENCE: 24

Arg Xaa Pro Trp Leu Leu
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Arg Val Tyr Ile His Pro Phe
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: neo-Trp

<400> SEQUENCE: 26

Asp Arg Val Trp Ile His Pro Phe
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Pro Pro Gly Phe Ser Pro Phe Arg
 1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: neo-Trp

<400> SEQUENCE: 28

Arg Pro Pro Gly Trp Ser Pro Phe Arg
 1               5
```

```
<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Gly Gly Phe Leu
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: neo-Trp

<400> SEQUENCE: 30

Trp Gly Gly Phe Leu
 1               5
```